(12) United States Patent
McGarrity et al.

(10) Patent No.: US 7,879,321 B2
(45) Date of Patent: *Feb. 1, 2011

(54) USE OF RNA TRANS-SPLICING FOR ANTIBODY GENE TRANSFER AND ANTIBODY POLYPEPTIDE PRODUCTION

(75) Inventors: Gerard J. McGarrity, Gaithersburg, MD (US); Mariano A. Garcia-Blanco, Durham, NC (US); Madaiah Puttaraju, Germantown, MD (US)

(73) Assignee: VIRxSYS Corporation, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/245,835

(22) Filed: Oct. 7, 2005

(65) Prior Publication Data

US 2006/0160182 A1  Jul. 20, 2006

Related U.S. Application Data

(60) Provisional application No. 60/617,012, filed on Oct. 8, 2004, provisional application No. 60/629,821, filed on Nov. 19, 2004.

(51) Int. Cl.
*A01N 63/00* (2006.01)
*C12N 15/09* (2006.01)

(52) U.S. Cl. .................. 424/93.2; 424/93.21; 536/23.1; 536/23.4; 536/23.53; 435/455

(58) Field of Classification Search ........................ None
See application file for complete search history.

(56) References Cited

U.S. PATENT DOCUMENTS

| | | | |
|---|---|---|---|
| 4,980,286 A | 12/1990 | Morgan et al. | |
| 5,354,678 A | 10/1994 | Lebkowski et al. | |
| 5,585,362 A | 12/1996 | Wilson et al. | |
| 5,589,377 A | 12/1996 | Lebkowski et al. | |
| 5,616,326 A | 4/1997 | Spibey | |
| 5,670,488 A | 9/1997 | Gregory et al. | |
| 5,700,470 A | 12/1997 | Saito et al. | |
| 5,731,172 A | 3/1998 | Saito et al. | |
| 5,747,072 A | 5/1998 | Davidson et al. | |
| 5,756,283 A | 5/1998 | Wilson et al. | |
| 5,789,390 A | 8/1998 | Descamps et al. | |
| 5,820,868 A | 10/1998 | Mittal et al. | |
| 5,837,484 A | 11/1998 | Trempe et al. | |
| 5,843,742 A | 12/1998 | Natsoulis et al. | |
| 5,851,806 A | 12/1998 | Kovesdi et al. | |
| 5,858,351 A | 1/1999 | Podsakoff et al. | |
| 5,869,037 A | 2/1999 | Crystal et al. | |
| 5,871,982 A | 2/1999 | Wilson et al. | |
| 5,877,011 A | 3/1999 | Armentano et al. | |
| 5,885,808 A | 3/1999 | Spooner et al. | |
| 5,891,690 A | 4/1999 | Massie | |
| 5,919,676 A | 7/1999 | Graham et al. | |
| 5,922,576 A | 7/1999 | He et al. | |
| 5,928,944 A | 7/1999 | Seth et al. | |
| 5,932,210 A | 8/1999 | Gregory et al. | |
| 5,952,221 A | 9/1999 | Kurtzman et al. | |
| 5,962,311 A | 10/1999 | Wickham et al. | |
| 5,962,313 A | 10/1999 | Podsakoff et al. | |
| 5,998,205 A | 12/1999 | Hallenbeck et al. | |
| 6,013,487 A | 1/2000 | Mitchell | |
| 6,083,702 A | 7/2000 | Mitchell et al. | |
| 6,150,141 A * | 11/2000 | Jarrell ..................... | 435/91.31 |
| 6,280,978 B1 | 8/2001 | Mitchell et al. | |
| 6,686,179 B2 * | 2/2004 | Fleer et al. ................ | 435/69.7 |

FOREIGN PATENT DOCUMENTS

| | | |
|---|---|---|
| WO | WO 88/09810 | 12/1988 |
| WO | WO 89/10134 | 11/1989 |
| WO | WO 98/11241 | 3/1998 |
| WO | WO 00/09734 | 2/2000 |

OTHER PUBLICATIONS

Nakabayashi et al. Biochem Biophy Res Comm Jun. 2004;318:773-85.*
U.S. Appl. No. 10/693,192, filed Oct. 23, 2003, "Screening Method for Identification of Efficient Pre-Trans-Splicing Molecules," Mitchell et al.
U.S. Appl. No. 10/434,727, filed May 8, 2003, "Use of Sliceosome Mediated RNA Trans-Splicing to Confer Cell Selective Replication to Adenoviruses," Otto et al.
U.S. Appl. No. 10/374,784, filed Feb. 25, 2003, "Trans-Splicing Mediated Imaging of Gene Expression," Mitchell et al.
U.S. Appl. No. 10/360,787, filed Jun. 5, 2002, "Spliceosome Mediated RNA Trans-Splicing for Correction of Factor VIII Genetic Defects," Mitchell et al.
U.S. Appl. No. 10/198,447, filed Jul. 17, 2002, "Spliceosome Mediated RNA Trans-Splicing for Correction of Skin Disorders," Mitchell et al.
U.S. Appl. No. 10/136,723, filed Apr. 30, 2002, "Transgenic Animal Model for Spliceosome-mediated RNA Trans-Splicing," Puttaraju et al.

(Continued)

*Primary Examiner*—Q. Janice Li
(74) *Attorney, Agent, or Firm*—Konstantina M. Katcheves; Saul Ewing VIRxSYS Corporation; Serge Sira, Esq

(57) ABSTRACT

The present invention provides methods and compositions for generating novel nucleic acid molecules through RNA trans-splicing that target a highly expressed pre-mRNA and contain the coding sequence for antibody polypeptide(s). The compositions of the invention include pre-trans-splicing molecules (PTMs) designed to interact with the target precursor messenger RNA molecule (target pre-mRNA) that is abundantly expressed or tumor specific and mediate a trans-splicing reaction resulting in the generation of novel chimeric RNA molecule (chimeric RNA) capable of encoding an antibody polypeptide. The invention provides for the in vivo production of chimeric RNA molecules that encode and result in the production of an antibody polypeptide that is therapeutically effective against, for example, infectious agents, cancer cells, transplantation antigens, rheumatoid arthritis, etc.

16 Claims, 19 Drawing Sheets

OTHER PUBLICATIONS

U.S. Appl. No. 10/103,294, filed Mar. 20, 2002, "Spliceosome Mediated RNA Trans-Splicing," Mitchell et al.
U.S. Appl. No. 10/075,028, filed Feb. 12, 2002, "Methods and Compositions for Use in Spliceosome Mediated RNA Trans-Splicing," Mitchell et al.
U.S. Appl. No. 10/076,248, filed Feb. 12, 2002, "Methods and Compositions for Use in Spliceosome Mediated RNA Trans-Splicing," Mitchell et al.
U.S. Appl. No. 09/838,858, filed Apr. 20, 2001, "Methods and Compositions for Use in Spliceosome Mediated RNA Trans-Splicing," Mansfield et al.
U.S. Appl. No. 09/756,097, filed Jan. 8, 2001, "Methods and Compositions for Use in Spliceosome Mediated RNA Trans-Splicing," Mitchell et al.
U.S. Appl. No. 09/756,095, filed Jan. 8, 2001, "Methods and Compositions for Use in Spliceosome Mediated RNA Trans-Splicing," Mitchell et al.
U.S. Appl. No. 09/756,096, filed Jan. 8, 2001, "Methods and Compositions for Use in Spliceosome Mediated RNA Trans-Splicing," Mitchell et al.
Bhaumik et al., "Molecular Imaging of Gene Expression in Living Subjects by Splicesome-Mediated RNA Trans-Splicing," Jun. 8, 2004, Proc. Natl. Acad. Sci., 101:23:8693-8698.
Tahara et al., "Trans-Splicing Repair of CD40-Ligand Deficiency Results in Naturally Regulated Correction of A Mouse Model of Hyper-IgM X-Linked Immunodeficiency," Aug. 2004, Nature Medicine, 10:835-841.
Chao et al., "Phenotype Correction of Hemophilia A Mice by Spliceosome-Mediated RNA Trans-Splicing," Aug. 2003, Nature Medicine, 9:1-5.
Liu et al., "Partial Correction of Endogenous Δ508 CFTR in Human Cystic Fibrosis Airway Epithelia by Spliceosome-Mediated RNA Trans-Splicing," Jan. 2002, Nature Biotechnology, 20:47-52.
Kim et al., "Role of the Nonsense-Mediated Decay Factor hUpf3 in the Splicing Dependent Exon-Exon Junction Complex," Sep. 7, 2001, Science 293:1832-1836.
Kirn et al., "Replication-Selective Virotherapy for Cancer:Biological Principles, Risk Management and Future Directions," Jul. 2001, Nat. Med. 7:781-787.
Tian et al., "Strong RNA Splicing Enhancers Identified by a Modified Method of Cycled Selection Interact with SR Protein," Sep. 7, 2001, J. Biological Chemistry 276:33833-33839.
Mansfield et al., "Repair of CFTR mRNA by Splicesome-Mediated RNA Trans-Splicing," Jul. 28, 2000, Gene Therapy 7:1885-1895.
Tacke et al., "Determinants of SR Protein Specificity," 1999, Curr. Opin. Cell Biol. 11:358-362.
He et al. "A Simplified System for Generating Recombinant Adenoviruses," Mar. 1998, Proc. Natl. Acad. Sci., 95, 2509-2514.
Lan et al., "Ribozyme-Mediated Repair of Sickle β-Globin mRNAs in Erythrocyte Precursors" Jun. 5, 1998, Science 280:1593-1596.
Phylactou et al., "Ribozyme-Mediated Trans-Splicing of a Trinucleotide Repeat" Apr. 1998, Nature Genetics 18:378-381.
Staley et al., "Mechanical Devices of the Spliceosome: Motors, Clocks, Springs and Things," 1998, Cell 92:315-326.
Bellet et al., "Malignant Transformation of Nontrophoblastic Cells is Associated With the Expression of Chorionic Gonadotropin β Genes Normally Transcribed Introphoblastic Cells," Feb. 1, 1997, Cancer Res. 57:516-523.
Coolidge et al., "Functional Analysis of The Polypyrimidine Tract in Pre-mRNA Splicing," 1997, Nucleic Acids Res. 25:888-896.
Crouzet et al. "Recombinational Construction in *Escherichia coli* of Infectious Adenoviral Genomes," Feb. 1997, Proc. Natl. Acad. Sci., 94, 1414-1419.
Good et al., "Expression of Small, Therapeutic RNAs in Human Cell Nuclei," 1997, Gene Ther. 4:45-54.
Malek et al., "Evolution of Trans-Splicing Plant Mitochondrial Introns in Pre-Permian Times," Jan. 1997, Proc. Nat'l. Acad. Sci., 94:553-558.
Chartier, et al., "Efficient Generation of Recombinant Adenovirus Vectors by Homologous Recombination in *Escherichia coli*," Jul. 1996, Virol. 70, 4805-4810.

Hoon et al., "Detection of Metastatic Breast Cancer by β-hCG Polymerase Chain Reaction," 1996, Int J. Cancer 69:369-374.
Jones et al., "Tagging Ribozyme Reaction Sites to Follow Trans-Splicing in Mammalian Cells," Jun. 1996, Nature Medicine 2:643-648.
Krämer A., "The Structure and Function of Proteins Involved in Mammalian Pre-mRNA Splicing," 1996, Annu. Rev. Biochem. 65:367-409.
Miyake et al. "Efficient Generation of Recombinant Adenoviruses Using Adenovirus DNA-Terminal Protein Complex and A Cosmid Bearing the Full-Length Virus Genome," Feb. 1996, Proc. Natl. Acad. Sci., 93, 1320-1324.
Nilsson et al., "Multiple Affinity Domains for the Detection, Purification, and Immobilization of Recombinant Proteins," 1996, J. Mol. Recognition, 9:585-594.
Pasman et al., "The 5' and 3' Splice Sites Come Together Via a Three Dimensional Diffusion Mechanism," 1996, Nucleic Acids Res. 24(9):1638-1645.
Boelens et al., "Nuclear Retention of RNA as a Mechanism for Localization" 1995, RNA 1:273-283.
Bruzik et al., "Enhancer-Dependent Interaction Between 5' and 3' Splice Sites in Trans," 1995, Proc. Nat'l. Acad. Sci., 92:7056-7059.
Chiara et al., "A Two-Step Mechanism for 5' and 3' Splice-Site Pairing," Jun. 1995, Nature 375:510-513.
Davis et al., "RNA Trans-Splicing in Flatworms," Sep. 15, 1995, J. Biol. Chem. 270:21813-21819.
Eul et al., "Experimental Evidence for RNA Trans-Splicing in Mammalian Cells," 1995, EMBO. J. 14(13):3226-3235.
Xiang-Dong Fu, "The Superfamily of Arginine/Serine-Rich Splicing Factors," 1995, RNA 1:663-680.
Bett et al. "An Efficient and Flexible System for Construction of Adenovirus Vectors with Insertions or Deletions in Early Regions 1 and 3," Sep. 1994, Proc. Natl., Acad. Sci., 91,8802-8806.
Hollenberg et al., "Multiple Promoter Elements in the Human Chorionic Gonadotropin B Subunit Genes Distinguish their Expression from Luteinizing Hormone β Gene," 1994, Mol. Cell Endo., 106:111-119.
Ketner et al. "Efficient Manipulation of the Human Adenovirus Genome as an Infectious Yeast Artificial Chromosome Clone," Jun. 1994, Proc. Natl. Acad. Sci., 91, 6186-6190.
Sullenger et al., "Ribozyme-Mediated Repair of Defective mRNA by Targeted Trans-Splicing," Oct. 1994, Nature 371:619-622.
Goldspiel et al., "Human Gene Therapy," Jul. 1993, Clinical Pharmacy 12:488-505.
Kozarsky and Wilson et al., "Gene Therapy: Adenovirus Vectors," 1993, Current Opinion in Genetics and Development 3:499-503.
Miller and Rosman, "Use of Retroviral Vectors for Gene Transfer and Expression," 1993, Meth. Enzymol. 217:581-599.
Moore and Sharp, "Evidence for Two Active Sites in the Splicesome Provided by Stereochemistry of Pre-mRNA Splicing," Sep. 23, 1993, The Nature, 365:364-368.
Moore et al, "Splicing of Precursors to mRNA by The Spliceosome," 1993, RNA World, 303-357.
Morgan and Anderson, "Human Gene Therapy," 1993, Ann. Rev. Biochem. 62:191-217.
Mulligan, Richard C., "The Basic Science of Gene Therapy," May 14, 1993, Science 260:926-932.
Roscigno et al., "A Mutational Analysis of the Polypyrimidine Tract of Introns," May 25, 1993, J. Bio. Chem., 268:11222-11229.
Tolstoshev, Paul, "Gene Therapy, Concepts, Current Trials, and Future Directions," 1993, Ann. Rev. Pharmacol. Toxicol. 33:573-596.
Acevedo et al., "Human Chorionic Gonadotropin-Beta Subunit Gene Expression in Cultured Human Fetal and Cancer Cells of Different Types and Origins," Oct. 15, 1995, Cancer 76:1467-1475.
Bruzik et al., "Spliced Leader RNAs from Lower Eukaryotes are Trans-spliced in Mammalian Cells," Dec. 1992, Nature 360:692-695.
Vellard et al., "A Potential Splicing Factor is Encoded by the Opposite Strand of The Trans-Spliced C-myb Exon," 1992, Proc. Nat'l. Acad. Sci., 89:2511-2515.
Dingwall and Laskey, "Nuclear Targeting Sequences—A Consensus?" Dec. 1991, Trends in Biochem. Sci., 16:478-481.

Ghattas et al., "The Encephalomyocarditis Virus Internal Ribosome Entry Site Allows Efficient Coexpression of Two Genes from a Recombinant Provirus in Culture Cells and in Embryos," Dec. 1991, Mol. Cell Biol. 11:5848-5859.

Janknecht et al., "Rapid and Efficient Purification of Native Histidine-Tagged Protein Expressed by Recombinant Vaccinia Virus," Jul. 8, 1991, Proc. Natl. Acad. Sci., 88:8972-8976.

Rosenfeld et al. "Adenovirus-Mediated Transfer of a Recombinant $\alpha\text{-}_1$ Antitrypsin Gene to the Lung Epithelium in Vivo," Apr. 19, 1991, Science, 252, 431-4.

Wu and Wu, "Delivery Systems for Gene Therapy," 1991, Biotherapy 3:87-95.

Gilardi et al. "Expression of Human $\alpha\text{-}_1$-Anti-trypsin Using a Recombinant Adenovirus Vector," 1990, EBS Lett. 267, 60-62.

Rajkovic et al., "A Spliced Leader is Present on a Subset of mRNAs from the Human Parasite *Schistosoma mansoni*" Nov. 1990, Proc. Nat'l. Acad. Sci., 87:8879-8883.

Schneider and Banes, "Building Blocks for Oligonucleotide Analogs with Dimethylene-Sulfide-Sulfoxide and Sulfone Groups Replacing Phosphodiester Linkages," 1990, Tet. Letters, 31:335-338.

Senapathy et al., "Splice Junctions, Branch Point Sites, and Exons:Sequence Statistics, Identification, and Applications to Genome Project," 1990, Methods in Enzymology, 183:252-278.

Uhlmann and Peyman, "Antisense Oligonucleotides: A New Therapeutic Principle," Jun. 1990, Chemical Reviews, 90:543-584.

Kerem et al., "Identification of the Cystic Fibrosis Gene: Genetic Analysis," Sep. 8, 1989, Science, 245:1073-1080.

Letsinger et al., "Cholesteryl-Conjugated Oligonucleotide: Synthesis, Properties, and Activity as Inhibitors of Replication of Human Immunodeficiency Virus in Cell Culture," Sep. 1989, Proc. Natl. Acad. Sci., 86:6553-6556.

Reed, Robin, "The Organization of 3' Splice Sites Sequences in Mammalian Introns," 1989, Genes Dev. 3:2113-2123.

Riordan et al., "Identification of the Cystic Fibrosis Gene: Cloning and Characterization of Complementary DNA," 1989, Science, 245:1066-1073.

Rommens et al., "Identification of the Cystic Fibrosis Gene: Chromosome Walking and Jumping," Sep. 8, 1989, Science, 245:1059-1065.

Shimizu et al., "Immunoglobulin Double-Isotype Expression by Trans-mRNA In a Human Immunoglobulin Transgenic Mouse," Oct. 1989, Proc. Nat'l. Acad. Sci. 86:8020-8023.

Smith et al., "Scanning From an Independently Specified Branch Point Defines the 3' Splice Site of Mammalian Introns," 1989, Nature, 342:243-247.

Van der Krol et al., "Modulation of Eukaryotic Gene Expression by Complementary RNA or DNA Sequences," 1988, BioTechniques, 6:958-976.

Reed & Maniatis, "The Role of The Mammalian Branchpoint Sequence In the Pre-mRNA Splicing," 1988, Genes Dev. 2:1268.

Smith et al, "Single-Step Purification of Polypeptides Expressed in *Escherichia coli* as Fusions with Glutathione S-Transferase," 1988, Gene, 67:31.

Zon et al., "Oligonucleotide Analogues as Potential Chemotherapeutic Agents," 1988, Pharm. Res., 5:539-549.

Krause M et al., "A Trans-Spliced Leader Sequence on Actin mRNA in *C. elegans*," 1987, Cell 49:753-761.

Lemaitre et al., "Specific Antiviral Activity of a Poly(L-lysine)-Conjugated Oligodeoxyribonucleotide Sequence Complementary to Vesicular Stomatitis Virus N Protein mRNA Initiation Site," 1987, Proc. Natl. Acad. Sci., 84:648-652.

Wu and Wu, "Receptor-Mediated in Vitro Gene Transformation by a Soluble DNA Carrier System," 1987, J. Biol. Chem., 262:429-4432.

Dingwall and Laskey, "Protein Import into the Cell Nucleus," 1986, Ann. Rev. Cell Biol. 2:367-390.

Murphy et al., "Identification of a Novel Y Branch Structure as an Intermediate in Trypanosome mRNA Processing: Evidence for Trans Splicing," 1986, Cell, 47:517.

Smith et al., "$M_r$, 26,000 Antigen of *Schistosoma japonicum* Recognized by Resistant WEH1 129/J Mice is a Parasite Glutathione S-Transferase," 1986, Proc. Natl. Acad. Sci., 83:8703-8707.

Sutton et al., "Evidence for Trans Splicing in Trypanosomes," 1986, Cell 47:527-535.

Konarska et al., "Trans Splicing of mRNA Precursors In Vitro" 1985, Cell 46:165-171.

Solnick et al, "Trans Splicing of mRNA Precursors," 1985, Cell 42:157-164.

Talmadge et al., "Only Three of the Seven Human Chorionic Gonadotropin Beta Subunit Genes can be Expressed in the Placenta," 1984, Nucleic Acids Res. 12:8415.

Accession No. K01722, Corynebacteriophage beta diptheria toxin (DT) gene, Apr. 27, 1993.

Berkner, et al. "Generation of Adenovirus by Transfection of Plasmids," 1983, Nucleic Acids Res. 11, 6003-6020.

Greenfield, "Nucleotide Sequence of the Structural Gene for the Diptheria Toxin Carried by Corynebacteriophage β," 1983, Proc. Natl. Acad. Sci., 80:6853-6857.

Brinster et al., "Regulation of Metallothionein-Thymidine Kinase Fusion Plasmids Injected into Mouse Eggs," 1982, Nature 296:39-42.

Benoist et al., "In Vivo Sequence Requirements of the SV40 Early Promoter Region," 1981, Nature, 290:304-310.

Wagner et al., "Nucleotide Sequence of the Thymidine Kinase Gene of Herpes Simplex Virus Type 1," Mar. 1981, Proc. Natl. Acad. Sci., 78(3):1441-1445.

Yamamoto et al., "Identification of a Functional Promoter in the Long Terminal Repeat of Rous Sarcoma Virus," 1980, Cell, 22:787-797.

Berget et al., Spliced Segments at the 5' Terminus of Adenovirus 2 Late mRNA, 1977, Proc. Natl. Acad. Sci., 74(8):3171-3175.

Chow et al., "An Amazing Sequence Arrangement at the 5' Ends of Adenovirus 2 Messenger RNA," 1977, Cell 12:1-8.

Graham et al., "Characteristics of a Human Cell Line Transformed by DNA from Human Adenovirus Type 5," 1977, J. Gen. Virol. 36:59-72.

Uchida et al, "Diptheria Toxin and Related Proteins: Isolation and Properties of Mutant Proteins Related to Diptheria Toxin," 1973 J. Biol. Chem., 248:3838.

Puttaraju et al., Spliceosome-Mediated RNA Trans-Splicing as a Tool for Gene Therapy, Nat. Biotech., 1999, vol. 17, 246-252.

Voss et al., "Efficiency Assessment of the Gene Trap Approach", 1998, Development Dynamics, 212:171-180.

Puttaraju et al., "Messenger RNA Repair and Restoration of Protein Function by Spliceosome-Mediated mRNA Trans-Splicing", Mol. Therapy, 2001, vol. 4, 105-114.

Song et al., "Intramuscular Administration of Recombinant Adeno-Associated Virus 2 α-1 Antitrypsin (rAAV-SERPINA1) Vectors in a Nonhuman Primate Model: Safety and Immunologic Aspects", Sep. 3, 2002, Molecular Therapy 6:329-335.

Garcia-Blanco et al, "Spliceosome-Mediated RNA trans-Splicing in Gene Therapy and Genomics," Apr. 20, 200, Gene Therapy and Regulation, 1:141-163.

Garcia-Blanco et al "Mending the Message", Nat. Biotech., 2003, vol. 21, No. 12, 1448-1449.

Liu et al., "Spliceosome-Mediated RNA trans-Splicing with Recombinant Adeno-Associated Virus Partially Restores Cystic Fibrosis Transmembrane Conductance Regulator Function to Polarized Human Cystic Fibrosis Airway Epithelial Cells," Sep. 2005 *Human Gene Therapy* 16:1116-1123.

Mansfield, et al. "5' Exon Replacement and Repair by Spliceosome-Mediated RNA trans-Splicing", RNA, 2003, vol. 9, 1290-1297.

Mansfield, et al., Repair of CFTR mRNA by Spliceosome-Mediated RNA Trans-Splicing, Gene Therapy, 2000, vol. 7, 1885-1895.

Manzano, et al., "Failure to Generate Atheroprotective Apolipoprotein A1 Phenotypes Using Synthetic RNA/DNA Oligonucleotides (chimeraplasts)", J. Gene Med., 2003, vol. 5, 795-802.

Parolini, et al., "Targeted Replacement of Mouse Apolipoprotein A-I with Human ApoA-I or the Mutant ApoA-I", J. Bio. Chem., 2003, vol. 278, 4740-4746.

Martinez-Sales, E., Internal Ribosome Entry Site Biology and Its Use In Expression Vectors, 1999, Current Opinion in Biology, 10:458-464.

Kikumori et al., "Promiscuity of Pre-mRNA Spliceosome-Meidated Trans Splicing: A Problem for Gene Therapy?," Jul. 20, 2001, Human Gene Therapy, 12:1429-1441.

U.S. Appl. No. 09/941,492, filed Aug. 29, 2001, "Methods and Compositions for Use in Spliceosome Mediated RNA Trans-Splicing," Mitchell et al.

U.S. Appl. No. 08/786,531, filed Jan. 21, 1997, "Vehicles for Stable Transfer of Green Fluorescent Protein Gene and Methods of Use For Same," Link. Jr., et al.

* cited by examiner

Figure 10

Mouse albumin signal pre peptide

ATG AAG TGG GTA ACC TTT CTC CTC CTC CTC TTC GTC TCC GGC TCT GCT TTT

Pro-peptide | coding → HPV-16 anti-E7 scFv (minus the first 7 nts)

TCC AGG GGT GTG TTT CGC CGA GGG AAC CTT AAG GAA GCA CAG GTC CAG CTG CAG GAG TCA GGG
GCT GAG GTG AAG CCT TCA GTG AAG GCT TGG GAG GTT AAA CTG TCC TGC AAG GCT TCT GGA TAC ACC TTC ACC AGC TAC TGG ATG AAC TGG GTG AAG CAG AGG CCT GGA CAT GGC CTT GAG AAG TGG ATT GGA GAG ATT TTA CCT GGA AGT GGT AGT ACT AAC TAC AAT GAG AAG TTC AAG GGC AAG GCC ACT CTG ACT GCA GAC AAA TCT TCC TCC ACA GCC TAC ATG CAA CTC AGC AGC CTG ACA TCT GAG GAC TCT GCC GTC TAT TAC TGT GCA AGA AGG GAC ACG TAC TGG TAC TTT GCT TAC TGG GGC CAA GGG ACC ACG ACC GTC TCC GGA GGC GGT TCA GGC GGA GGT GGC Linker
TCT GGT GGC TCT CCA GGA AAG GTC ACT ATC ACC TCT CCA GCA ATC ATG Light chain
GCT GCA AGT TCC AGC AGT GTC AGT TAC ATG TAC TGG TAC CAG CAG AAG CCA GGA TCC TCC CCC AAA CCC TGG ATT TAT GGC ACA TCC AAC CTG GCT TCT GGA GTC CCT GTT CGC TTC AGT GGC AGT GGA TCT GGG ACC TCT TAC TCT CTC ACA ATC AGC AGC ATG GAG GCT GAA GAT GCT GCC ACT TAT TAC TGT CAA CAG TGG AGT AGT TAC CCA CTC ACG TTC GGT GCT GGG ACC AAG CTG GAA ATA AAA CGG GAC TAC AAA GAC
GAT GAC GAC AAG TGA FLAG tag
stop codon

SEQ ID NO. 22

Production of HPV16 anti-E7 scFv in Mice

Western Results

SEQUENCE LISTING

<160> NUMBER OF SEQ ID NOS: 25

<210> SEQ ID NO 1
<211> LENGTH: 8
<212> TYPE: RNA
<213> ORGANISM: Unknown
<220> FEATURE:
<223> OTHER INFORMATION: Unable to Identify

<400> SEQUENCE: 1 agguragu                                                                 8

<210> SEQ ID NO 2
<211> LENGTH: 7
<212> TYPE: RNA
<213> ORGANISM: Unknown
<220> FEATURE:
<223> OTHER INFORMATION: Unable to Identify
<220> FEATURE:
<221> NAME/KEY: misc_feature
<222> LOCATION: (2)..(2)
<223> OTHER INFORMATION: n is a, c, g, or u

<400> SEQUENCE: 2 ynyurac                                                                  7

<210> SEQ ID NO 3
<211> LENGTH: 258
<212> TYPE: DNA
<213> ORGANISM: Unknown
<220> FEATURE:
<223> OTHER INFORMATION: Unable to Identify

<400> SEQUENCE: 3
gtagttcttt tgttcttcac tattaagaac ttaatttggt gtccatgtct cttttttttt      60
ctagtttgta gtgctggaag gtattttggg agaaattctt acatgagcat taggagaatg     120
tatgggtgta gtgtcttgta taatagaaat tgttccactg ataatttact ctagtttttt     180

```
atttcctcat attattttca gtggcttttt cttccacatc tttatatttt gcaccacatt    240
caacactgta gcggccgc                                                  258
```

<210> SEQ ID NO 4
<211> LENGTH: 270
<212> TYPE: DNA
<213> ORGANISM: Unknown
<220> FEATURE:
<223> OTHER INFORMATION: Unable to Identify

<400> SEQUENCE: 4

```
ccaactatct gaatcatgtg cccttctct gtgaacctct atcataatac ttgtcacact     60
gtattgtaat tgtctctttt actttcccct gtatcttttg tgcatagcag agtacctgaa    120
acaggaagta ttttaaatat tttgaatcaa atgagttaat agaatcttta caaataagaa    180
tatacacttc tgcttaggat gataattgga ggcaagtgaa tcctgagcgt gatttgataa    240
tgacctaata atgatgggtt ttatttccag                                     270
```

<210> SEQ ID NO 5
<211> LENGTH: 18
<212> TYPE: RNA
<213> ORGANISM: Unknown
<220> FEATURE:
<223> OTHER INFORMATION: Unable to Identify

<400> SEQUENCE: 5

```
gggcugauuu uuccaugu                                                  18
```

<210> SEQ ID NO 6
<211> LENGTH: 23
<212> TYPE: DNA
<213> ORGANISM: Unknown
<220> FEATURE:
<223> OTHER INFORMATION: Unable to Identify

<400> SEQUENCE: 6

```
taatacgact cactataggg aga                                            23
```

<210> SEQ ID NO 7
<211> LENGTH: 23
<212> TYPE: DNA
<213> ORGANISM: Unknown
<220> FEATURE:
<223> OTHER INFORMATION: Unable to Identify
<220> FEATURE:
<221> NAME/KEY: misc_feature
<222> LOCATION: (22)..(22)
<223> OTHER INFORMATION: n is a, c, g, or t

<400> SEQUENCE: 7

```
atttaggtga cactatagaa gng                                            23
```

<210> SEQ ID NO 8
<211> LENGTH: 23
<212> TYPE: DNA
<213> ORGANISM: Unknown
<220> FEATURE:
<223> OTHER INFORMATION: Unable to Identify

<400> SEQUENCE: 8

```
aattaaccct cactaaaggg aga                                            23
```

<210> SEQ ID NO 9

```
<211> LENGTH: 115
<212> TYPE: DNA
<213> ORGANISM: Unknown
<220> FEATURE:
<223> OTHER INFORMATION: Unable to Identify

<400> SEQUENCE: 9
gctagcatga agtgggtaac ctttctcctc ctcctcttcg tctccggctc tgcttttcc      60 aggggtgtgt ttcgccgaga agcacaggtc caactgcagg agtcaggggc tgagc         115

<210> SEQ ID NO 10
<211> LENGTH: 115
<212> TYPE: DNA
<213> ORGANISM: Unknown
<220> FEATURE:
<223> OTHER INFORMATION: Unable to Identify

<400> SEQUENCE: 10
gctcagcccc tgactcctgc agttggacct gtgcttctcg gcgaaacaca ccctggaaa      60 aagcagagcc ggagacgaag aggaggagga gaaaggttac ccacttcatg ctagc         115

<210> SEQ ID NO 11
<211> LENGTH: 28
<212> TYPE: DNA
<213> ORGANISM: Unknown
<220> FEATURE:
<223> OTHER INFORMATION: Unable to Identify

<400> SEQUENCE: 11
gctagcatgg cccaggtcca actgcagg                                        28

<210> SEQ ID NO 12
<211> LENGTH: 59
<212> TYPE: DNA
<213> ORGANISM: Unknown
<220> FEATURE:
<223> OTHER INFORMATION: Unable to Identify

<400> SEQUENCE: 12
aagctttcac ttgtcgtcat cgtctttgta gtcccgtttt atttccgctt ggtcccagc      59

<210> SEQ ID NO 13
<211> LENGTH: 23
<212> TYPE: DNA
<213> ORGANISM: Unknown
<220> FEATURE:
<223> OTHER INFORMATION: Unable to Identify

<400> SEQUENCE: 13
acctttctcc tcctcctctt cgt                                             23

<210> SEQ ID NO 14
<211> LENGTH: 22
<212> TYPE: DNA
<213> ORGANISM: Unknown
<220> FEATURE:
<223> OTHER INFORMATION: Unable to Identify

<400> SEQUENCE: 14
agtaagcaaa ccagtagccg tc                                              22

<210> SEQ ID NO 15
<211> LENGTH: 6
<212> TYPE: DNA
<213> ORGANISM: Unknown
```

```
<220> FEATURE:
<223> OTHER INFORMATION: Unable to Identify

<400> SEQUENCE: 15 gctagc                                                                    6

<210> SEQ ID NO 16
<211> LENGTH: 6
<212> TYPE: RNA
<213> ORGANISM: Unknown
<220> FEATURE:
<223> OTHER INFORMATION: Unable to Identify

<400> SEQUENCE: 16 ccgcgg                                                                    6

<210> SEQ ID NO 17
<211> LENGTH: 45
<212> TYPE: DNA
<213> ORGANISM: Unknown
<220> FEATURE:
<223> OTHER INFORMATION: Unable to Identify

<400> SEQUENCE: 17
tactaactca atttttttt tttttttttt aattaacagg atgca                         45

<210> SEQ ID NO 18
<211> LENGTH: 79
<212> TYPE: DNA
<213> ORGANISM: Unknown
<220> FEATURE:
<223> OTHER INFORMATION: Unable to Identify

<400> SEQUENCE: 18
atgaagtggg taacctttct cctcctcctc ttcgtctccg gctctgcttt ttccaggggt        60
gtgtttcgcc gagaagcac                                                    79

<210> SEQ ID NO 19
<211> LENGTH: 79
<212> TYPE: DNA
<213> ORGANISM: Unknown
<220> FEATURE:
<223> OTHER INFORMATION: Unable to Identify

<400> SEQUENCE: 19
atgaagtggg taacctttct cctcctcctc ttcgtctccg gctctgcttt ttccaggggt        60
gtgtttcgcc gagaagcac                                                    79

<210> SEQ ID NO 20
<211> LENGTH: 30
<212> TYPE: DNA
<213> ORGANISM: Unknown
<220> FEATURE:
<223> OTHER INFORMATION: Unable to Identify

<400> SEQUENCE: 20
gaagcacagg tccaactgca ggagtcaggg                                        30

<210> SEQ ID NO 21
<211> LENGTH: 30
<212> TYPE: DNA
<213> ORGANISM: Unknown
<220> FEATURE:
<223> OTHER INFORMATION: Unable to Identify
```

<400> SEQUENCE: 21
atggcccagg tccaactgca ggagtcaggg                                 30

<210> SEQ ID NO 22
<211> LENGTH: 831
<212> TYPE: DNA
<213> ORGANISM: Unknown
<220> FEATURE:
<223> OTHER INFORMATION: Unable to Identify

<400> SEQUENCE: 22
atgaagtggg taacctttct cctcctcctc ttcgtctccg gctctgcttt ttccaggggt    60
gtgtttcgcc gagaagcaca ggtccaactg caggagtcag ggctgagct tgtgaagcct    120 ggggcttcag tgaagctgtc ctgcaaggct tctggctaca ccttcaccag ctactggatg   180
cactgggtga acagaggcc tggacatggc cttgagtgga ttggagagat tttacctgga    240
agtggtagta ctaactacaa tgagaagttc aagggcaagg ccacattcac tgcagataca   300
tcctccaaca cagcctacat gcaactcagc agcctgacat ctgaggactc tgccgtctat   360
tactgtgcaa gaaggacgga cggctactgg tttgcttact ggggccaagg gaccacggtc   420
accgtctcct caggtggagg cggttcaggc ggaggtggct ctggcggtgg cggatcggac   480
atcgagctca ctcagtctcc agcaatcatg gctgcatctc aggggagaa ggtcaccatc    540 acctgcagtg tcagctcaag tataagttcc agcaacttgc actggtacca gcagaagtca   600
gaaacctccc ccaaaccctg gatttatggc acatccaacc tggcttctgg agtccctgtt   660
cgcttcagtg gcagtggatc tgggacctct tattctctca caatcagcag catggaggct   720
gaagatgctg ccacttatta ctgtcaacag tggagtagtt acccactcac gttcggtgct   780
gggaccaagc tggaaataaa acgggactac aaagacgatg acgacaagtg a            831

<210> SEQ ID NO 23
<211> LENGTH: 11
<212> TYPE: DNA
<213> ORGANISM: Unknown
<220> FEATURE:
<223> OTHER INFORMATION: Unable to Identify

<400> SEQUENCE: 23
tattaataca g                                                    11

<210> SEQ ID NO 24
<211> LENGTH: 79
<212> TYPE: DNA
<213> ORGANISM: Unknown
<220> FEATURE:
<223> OTHER INFORMATION: Unable to Identify

<400> SEQUENCE: 24
gctagcbdcc gcggacgatc tcatattcta tcgtcgaata ctaactttt ttttttttt     60 taattaacag ccccccaga                                            79

<210> SEQ ID NO 25
<211> LENGTH: 23
<212> TYPE: DNA
<213> ORGANISM: Unknown

-continued

```
<220> FEATURE:
<223> OTHER INFORMATION: Unable to Identify

<400> SEQUENCE: 25
tttaattaac ataggtccaa ctg                                              23
```

USE OF RNA TRANS-SPLICING FOR ANTIBODY GENE TRANSFER AND ANTIBODY POLYPEPTIDE PRODUCTION

CROSS REFERENCE TO RELATED APPLICATION

The present application claims benefit under 35 U.S.C. §119 to U.S. Provisional Patent Application No. 60/617,012 filed on Oct. 8, 2004 and U.S. Provisional Patent Application No. 60/629,821 filed on Nov. 19, 2004, the disclosures of which are hereby incorporated by reference in their entity.

INTRODUCTION

The present invention provides methods and compositions for generating novel nucleic acid molecules through RNA trans-splicing that target a highly expressed and/or tumor specific or associated pre-mRNA and contain the coding sequence of an antibody polypeptide. The compositions of the invention include pre-trans-splicing molecules (PTMs) designed to interact with the target precursor messenger RNA molecule (target pre-mRNA) that is abundantly expressed, and mediate a trans-splicing reaction resulting in the generation of novel chimeric RNA molecule (chimeric RNA) capable of encoding an antibody polypeptide. The purpose of the invention is to develop in vivo production of physiologically and/or clinically effective levels of chimeric RNA molecules that encode and result in the production of an antibody polypeptide that is effective against, for example, infectious agents, cancer cells, transplantation antigens, rheumatoid arthritis, etc. The methods and compositions of the present invention can be used to confer immunity against a variety of different immunogens/antigens. Such immunogens/antigens include, but are not limited to, those encoded for by infectious agents, such as viral, for example HIV, bacterial, fungal or parasitic agents. The target pre-mRNA may be abundant transcripts, such as those encoding albumin or casein. The target pre-mRNA may also be a tumor-specific and/or tumor-associated transcript. Additionally, the antibody encoded in the PTM could target a tumor-specific and/or tumor-associated antigen or an antigen expressed in autoimmune disease.

In addition, the present invention may be used to produce physiologically and/or clinically effective amounts of an antibody polypeptide or polypeptides in vitro by targeting an abundantly expressed pre-mRNA in, e.g., cell culture.

The compositions of the invention further include recombinant vector systems capable of expressing the PTMs of the invention and cells expressing said PTMs. The methods of the invention encompass contacting the PTMs of the invention with an abundantly expressed pre-mRNA under conditions in which a portion of the PTM is trans-spliced to a portion of the abundantly expressed pre-mRNA to form a chimeric RNA molecule that would express an antibody polypeptide. The methods and compositions of the present invention can be used to target specific molecules, receptors and/or cell types.

BACKGROUND OF THE INVENTION

RNA Splicing

DNA sequences in the chromosome are transcribed into pre-mRNAs that contain coding regions (exons) and generally also contain intervening non-coding regions (introns). Introns are removed from pre-mRNAs in a precise process called cis-splicing (Chow et al., 1977, Cell 12: 1-8; and Berget, S. M. et al., 1977, Proc. Natl. Acad. Sci. USA 74: 3171-3175). Splicing takes place as a coordinated interaction of several small nuclear ribonucleoprotein particles (snRNP's) and many protein factors that assemble to form an enzymatic complex known as the spliceosome (Moore et al., 1993, in The RNA World, R. F. Gestland and J. F. Atkins eds. (Cold Spring Harbor Laboratory Press, Cold Spring Harbor, N.Y.); Kramer, 1996, Annu. Rev. Biochem., 65: 367-404; Staley and Guthrie, 1998, Cell 92: 315-326).

In most cases, the splicing reaction occurs within the same pre-mRNA molecule, which is termed cis-splicing. Splicing between two independently transcribed pre-mRNAs is termed trans-splicing. (See FIG. 1) Trans-splicing was first discovered in trypanosomes (Sutton & Boothroyd, 1986, Cell 47: 527; Murphy et al., 1986, Cell 47: 517) and subsequently in nematodes (Krause & Hirsh, 1987, Cell 49: 753); flatworms (Rajkovic et al., 1990, Proc. Nat'l. Acad. Sci. USA, 87: 8879; Davis et al., 1995, J. Biol. Chem. 270: 21813) and in plant mitochondria (Malek et al., 1997, Proc. Nat'l. Acad. Sci. USA 94: 553). In the parasite Trypanosoma brucei, all mRNAs acquire a splice leader (SL) RNA at their 5' termini by trans-splicing. A 5' leader sequence is also trans-spliced onto some genes in Caenorhabditis elegans. This mechanism is appropriate for adding a single common sequence to many different transcripts.

The mechanism of splice leader trans-splicing, which is nearly identical to that of conventional cis-splicing, proceeds via two phosphoryl transfer reactions. The first causes the formation of a 2'-5' phosphodiester bond producing a 'Y' shaped branched intermediate, equivalent to the lariat intermediate in cis-splicing. The second reaction, exon ligation, proceeds as in conventional cis-splicing. In addition, sequences at the 3' splice site and some of the snRNPs, which catalyze the trans-splicing reaction, closely resemble their counterparts involved in cis-splicing.

Trans-splicing may also refer to a different process, where an intron of one pre-mRNA interacts with an intron of a second pre-mRNA, enhancing the recombination of splice sites between two conventional pre-mRNAs. This type of trans-splicing was postulated to account for transcripts encoding a human immunoglobulin variable region sequence linked to the endogenous constant region in a transgenic mouse (Shimizu et al., 1989, Proc. Nat'l. Acad. Sci. USA 86: 8020). In addition, trans-splicing of c-myb pre-RNA has been demonstrated (Vellard, M. et al. Proc. Nat'l. Acad. Sci., 1992 89: 2511-2515) and more recently, RNA transcripts from cloned SV40 trans-spliced to each other were detected in cultured cells and nuclear extracts (Eul et al., 1995, EMBO. J. 14: 3226). However, naturally occurring trans-splicing of mammalian pre-mRNAs is thought to be a rare event (Flouriot G. et al., 2002 J. Biol. Chem: Finta, C. et al., 2002 J. Biol Chem 277: 5882-5890).

In vitro trans-splicing has been used as a model system to examine the mechanism of splicing by several groups (Konarska & Sharp, 1985, Cell 46: 165-171 Solnick, 1985, Cell 42: 157; Chiara & Reed, 1995, Nature 375: 510; Pasman and Garcia-Blanco, 1996, Nucleic Acids Res. 24: 1638). Reasonably efficient trans-splicing (30% of cis-spliced analog) was achieved between RNAs capable of base pairing to each other, splicing of RNAs not tethered by base pairing was further diminished by a factor of 10. Other in vitro trans-splicing reactions not requiring obvious RNA-RNA interactions among the substrates were observed by Chiara & Reed (1995, Nature 375: 510), Bruzik J. P. & Maniatis, T. (1992, Nature 360: 692) and Bruzik J. P. and Maniatis, T., (1995, Proc. Nat'l. Acad. Sci. USA 92: 7056-7059). These reactions occur at relatively low frequencies and require specialized elements, such as a downstream 5' splice site or exonic splicing enhancers.

In addition to splicing mechanisms involving the binding of multiple proteins to the precursor mRNA which then act to correctly cut and join RNA, a third mechanism involves cutting and joining of the RNA by the intron itself, by what are termed catalytic RNA molecules or ribozymes. The cleavage activity of ribozymes has been targeted to specific RNAs by engineering a discrete "hybridization" region into the ribozyme. Upon hybridization to the target RNA, the catalytic region of the ribozyme cleaves the target. It has been suggested that such ribozyme activity would be useful for the inactivation or cleavage of target RNA in vivo, such as for the treatment of human diseases characterized by production of foreign of aberrant RNA. In such instances small RNA molecules are designed to hybridize to the target RNA and by binding to the target RNA prevent translation of the target RNA or cause destruction of the RNA through activation of nucleases. The use of antisense RNA has also been proposed as an alternative mechanism for targeting and destruction of specific RNAs.

Using the Tetrahymena group I ribozyme, targeted trans-splicing was demonstrated in $E.$ $coli.$ (Sullenger B. A. and Cech. T. R., 1994, $Nature$ 341: 619-622), in mouse fibroblasts (Jones, J. T. et al., 1996, $Nature Medicine$ 2: 643-648), human fibroblasts (Phylacton, L. A. et al. $Nature Genetics$ 18: 378-381) and human erythroid precursors (Lan et al., 1998, $Science$ 280: 1593-1596). For a review of clinically relevant technologies to modify RNA, see Sullenger and Gilboa, 2002 $Nature$ 418: 252-8. The present invention relates to the use of targeted trans-splicing mediated by native mammalian splicing machinery, i.e., spliceosomes, to reprogram or alter the coding sequence of a targeted mRNA.

U.S. Pat. Nos. 6,083,702, 6,013,487 and 6,280,978 describe the general use of PTMs to mediate a trans-splicing reaction by contacting a target precursor mRNA to generate novel chimeric RNAs.

Antibodies

Therapeutic antibodies are genetically engineered antibodies designed to be highly specific for disease targets (Brekke and Sandlie. Therapeutic antibodies for human diseases at the dawn of the twenty first century. 2003, $Nature Reviews Drug Discovery$ 2: 52-62). It is a form of therapy that seeks to eliminate, attenuate or prevent a pathogenic infection or disease target, such as bacterial, viral or tumor cell targets.

The use of therapeutic antibodies is based on the structure of a typical antibody, or immunoglobulin. An antibody comprises a constant (Fc) region and two antigen-binding, variable (Fab) regions, formed by two pairs of polypeptide chains (heavy and light). The N-terminal end of the heavy and light chain polypeptides form the antigen-binding, variable portion of the antibody. The light and heavy chain variable regions can associate to form an antigen-binding region ($F_v$). The variable region is responsible for binding to the specific antigen in question, and the constant region is responsible for biological effector responses such as complement binding, etc. The constant regions are not necessary for antigen binding and may be separated from the antibody molecule to obtain biologically active (i.e., binding) variable regions. Single chain antibodies may be created by incorporating individual variable regions into a single polypeptide chain. As a result, the single chain antibody will have binding specificity and affinity similar to that of the corresponding fragments.

While the Fab and Fv portions bind to potential therapeutic targets, the Fc portion may bind to potential effector molecules of the immune system, such as the complement system and Fc receptors on cells. Because antibodies are highly specific molecules capable of recognizing various pathogenic and disease antigens, they are being developed as potent agents to fight diseases, such as cancer, autoimmune diseases and infection.

Therapeutic antibodies function by three mechanisms of action: blocking the action of specific molecules, targeting specific cells, and functioning as signaling molecules (Brekke and Sandlie. Therapeutic antibodies for human diseases at the dawn of the twenty first century. 2003, $Nature Reviews Drug Discovery$ 2: 52-62). The antibodies can be designed to target soluble factors, such as cytokines, from reaching their cellular target and blocking the effect of the soluble factor (Brekke and Sandlie. Therapeutic antibodies for human diseases at the dawn of the twenty first century. 2003, $Nature Reviews Drug Discovery$ 2: 52-62). The antibodies can also be designed to target receptors on specific cell types, and carry various effector moieties, such as toxins, to a specific population of cells to exert a specific cytotoxic effect (Brekke and Sandlie. Therapeutic antibodies for human diseases at the dawn of the twenty first century. 2003, $Nature Reviews Drug Discovery$ 2:52-62). Lastly, the variable portion can be designed to act as a signaling agent, for example as an agonist in activation of cell populations or crosslinking cell surface receptors (Brekke and Sandlie. Therapeutic antibodies for human diseases at the dawn of the twenty first century. 2003, $Nature Reviews Drug Discovery$ 2: 52-62).

Serum therapy has been used in the treatment of various infectious diseases, such as anthrax, small pox, meningitis and the plague. It has been known since the 1890's that specific antibodies could protect against bacterial toxins. The presence of specific antibodies to bacterial targets and toxins act through passive immunity to confer protection on the subject. Passive immunity is a form of immunity in which antibodies against a disease are acquired naturally (as through the placenta to an unborn child) or artificially (as by administration of antiserum). Passive immunization is advantageous over the administration of antimicrobial agents, such as antibiotics, due to its low toxicity and highly specific activity towards the target (Brekke and Sandlie. Therapeutic antibodies for human diseases at the dawn of the twenty first century. 2003, $Nature Reviews Drug Discovery$ 2: 52-62). Therapeutic antibodies may be administered as serum or expressed in vivo.

A recent review of the field of therapeutic antibody gene transfer notes that while pre-clinical results in this field have been promising, overall serum levels of antibodies have been, at best, in the low therapeutic range in animal models (Bakker, J. M., Bleeker, W. K. and Parren, P. W. H. I. Therapeutic antibody gene transfer: an active approach to passive immunity. 2004, $Molecular Therapy$ 10: 411-416). The major concern noted by the authors is the ability to produce therapeutically effective plasma levels. Another concern is whether viral vectors could have long-term adverse effects due to the inability to control gene expression when delivered by viral vectors. While antibody concentrations in plasma will vary for different applications, concentrations above 3-30 ug/ml would generally be required. It has been reported that concentrations of 40 ug/ml are required to protect infants against respiratory syncytial virus (Zaaijer, H. L., et al., Ther. Drug Monitor. 24: 444-445, 2002).

It is estimated that a plasma level of 1 ug/ml corresponds to an immunoglobulin production of about 25 ug/kg/day in mice (Bakker, J. M., Bleeker, W. K. and Parren, P. W. H. I. Therapeutic antibody gene transfer: an active approach to passive immunity. 2004, $Molecular Therapy$ 10: 411-416). Plasma levels of immunoglobulin in humans would be expected to be higher due to the longer half life in humans (21 days) in comparison to mouse (4 days).

There remains a need in the art for the development of a method to produce in vivo, in a subject, PTMs and proteins comprising antigenic peptides with an effective serum concentration that enables safe, efficient and effective use of the PTMs in the treatment of disorders and diseases, such as infection, cancer, rheumatoid arthritis, etc. The present invention addresses this need by introducing gene sequences that encode single chain antibodies and splicing them to an abundantly expressed pre-mRNA target. The abundant expression of a gene, such as albumin, casein or a tumor-specific protein, will result in levels of immunoglobulin molecules that will be effective against specific targets, such as infectious organisms, cancer cells or cells that express self antigens. In particular, the potency of albumin mRNA is illustrated by the fact that albumin represents 54% of serum proteins in humans, having a concentration of 33-50 mg/ml (Anderson and Anderson. Molec. Cell Proteomics 2002 1: 845).

SUMMARY OF THE INVENTION

The present invention relates to compositions and methods for generating novel therapeutic and prophylactic nucleic acid molecules through targeted trans-splicing. The compositions of the invention include pre-trans-splicing molecules (hereinafter referred to as "PTMs") designed to interact with a target pre-mRNA molecule (hereinafter referred to as "pre-mRNA"), and mediate a trans-splicing reaction resulting in the generation of a novel chimeric RNA molecule comprising sequences encoding an antibody polypeptide. The methods of the invention encompass contacting the PTMs of the invention with target pre-mRNA under conditions in which a portion of the PTM is trans-spliced to the target pre-mRNA to form a chimeric mRNA comprising sequences encoding an antibody polypeptide. The PTMs of the invention are genetically engineered so that the chimeric mRNA comprising sequences encoding an antibody polypeptide resulting from the trans-splicing reaction is capable of being translated to produce the antibody polypeptide. The target pre-mRNA may be an abundantly expressed transcript, such as albumin, or a tumor associated or tumor-specific antigen. The disclosures of all references cited herein are hereby incorporated by reference in their entirety.

BRIEF DESCRIPTION OF THE DRAWINGS

FIG. 10 shows a nucleotide sequence of the trans-spliced mouse albumin-HPV16 anti-E7 scFv mRNA.

DETAILED DESCRIPTION OF THE INVENTION

The present invention relates to novel compositions comprising pre-trans-splicing molecules (PTMs), designed for spliceosome mediated RNA trans-splicing, and the use of such molecules for generating a novel chimeric RNA molecule comprising sequences encoding an antibody polypeptide.

In some embodiments, the present invention may be used for the in vivo production of chimeric RNA molecules that encode and result in the production of antibody polypeptides and recombinant proteins that are effective against, for example, infectious agents, cancer cells, transplantation antigens, etc. In additional embodiments, the present invention may be used to produce antibody polypeptides in vitro, for example by producing the chimeric RNA and translating it in cell culture.

Figure 1:
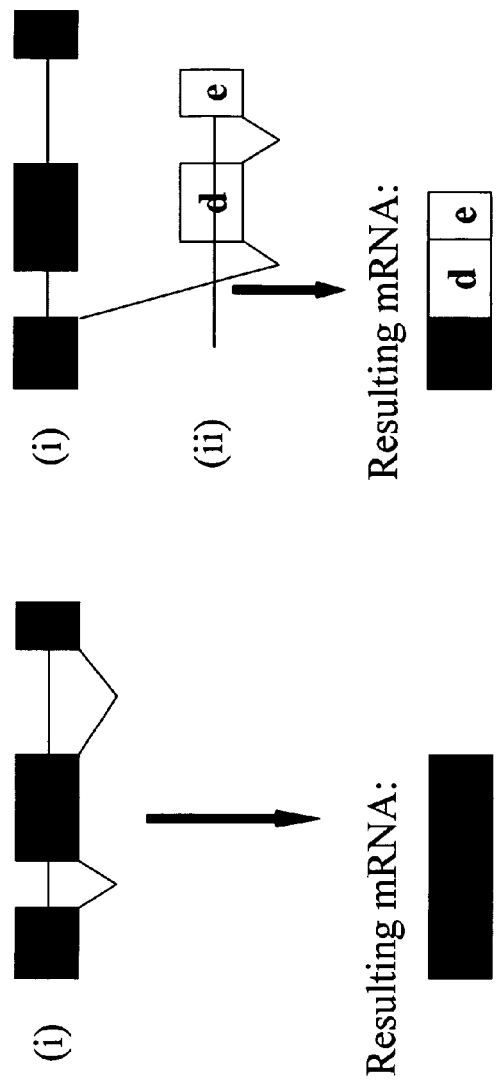
FIG. 1a shows a schematic representation of cis-splicing reactions.
FIG. 1b shows a schematic representation of trans-splicing reactions.
Figure 2:
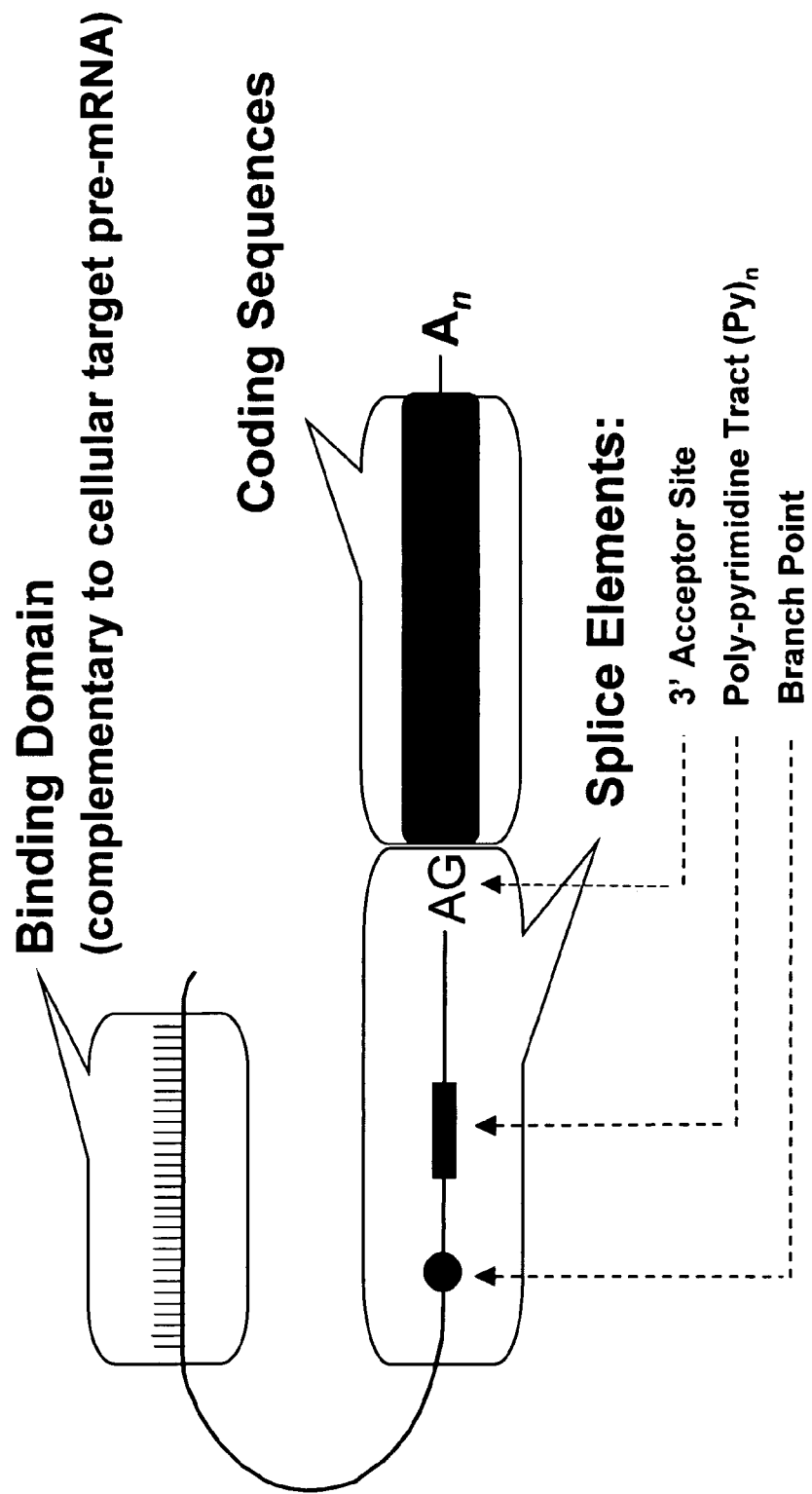
FIG. 2 shows a schematic representation of pre-trans-splicing molecules (PTMs).

The PTMs of the invention, for use in spliceosome mediated trans-splicing, comprise (i) one or more target binding domains that are designed to specifically bind to a target pre-mRNA, (ii) a 3' splice region that includes a 3' splice acceptor site and/or a 5' splice donor site; and (iii) nucleotide sequences encoding an antibody polypeptide. The PTM may further comprise a branchpoint, a pyrimidine tract and one or more spacer regions that separate the splice sites from the target-binding domain. (See FIG. 2)

Figure 3:
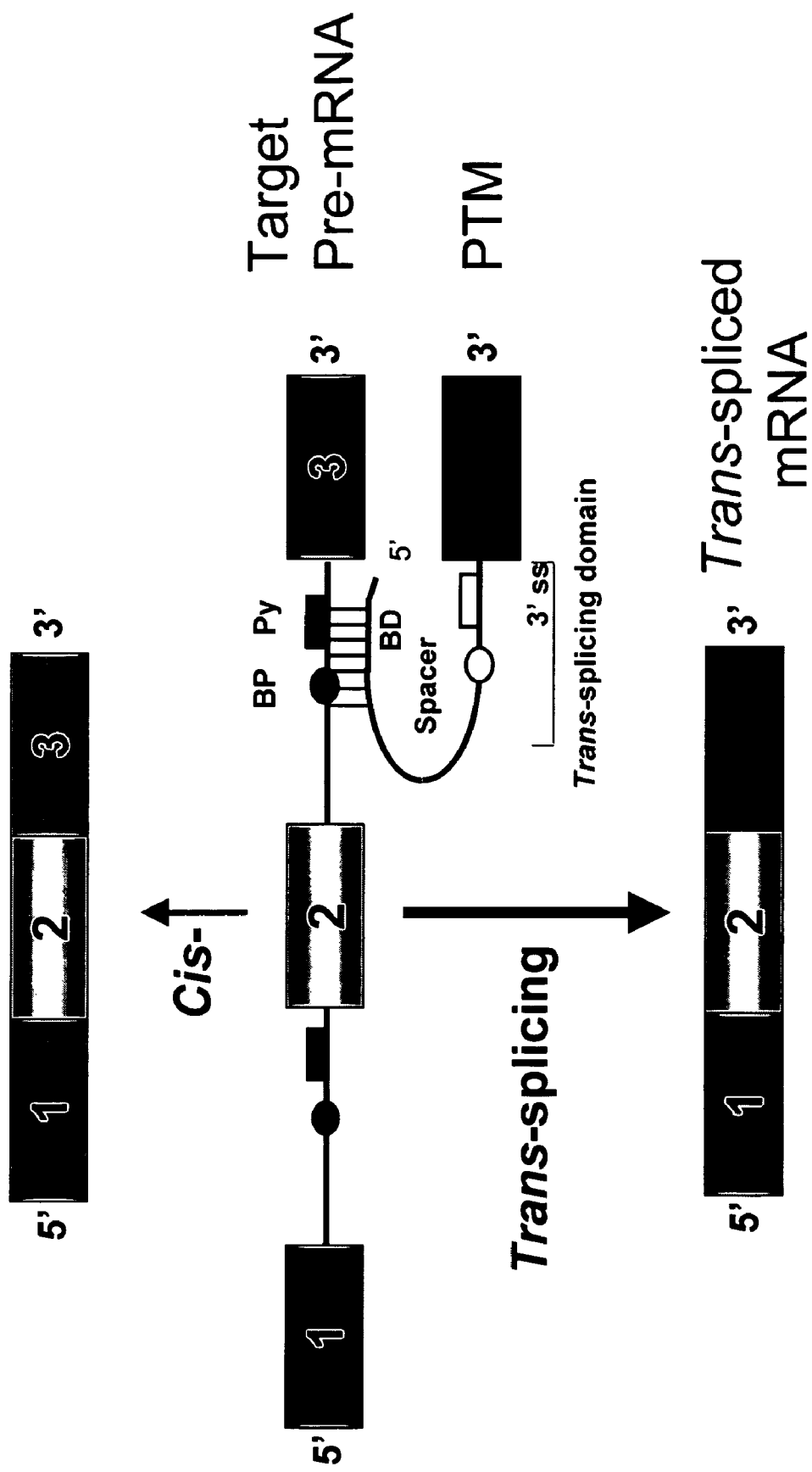
FIG. 3 shows a schematic representation of a trans-splicing reaction between the target 5' splice site and PTM's 3' splice site and 3' exon replacement.
Figure 4A:
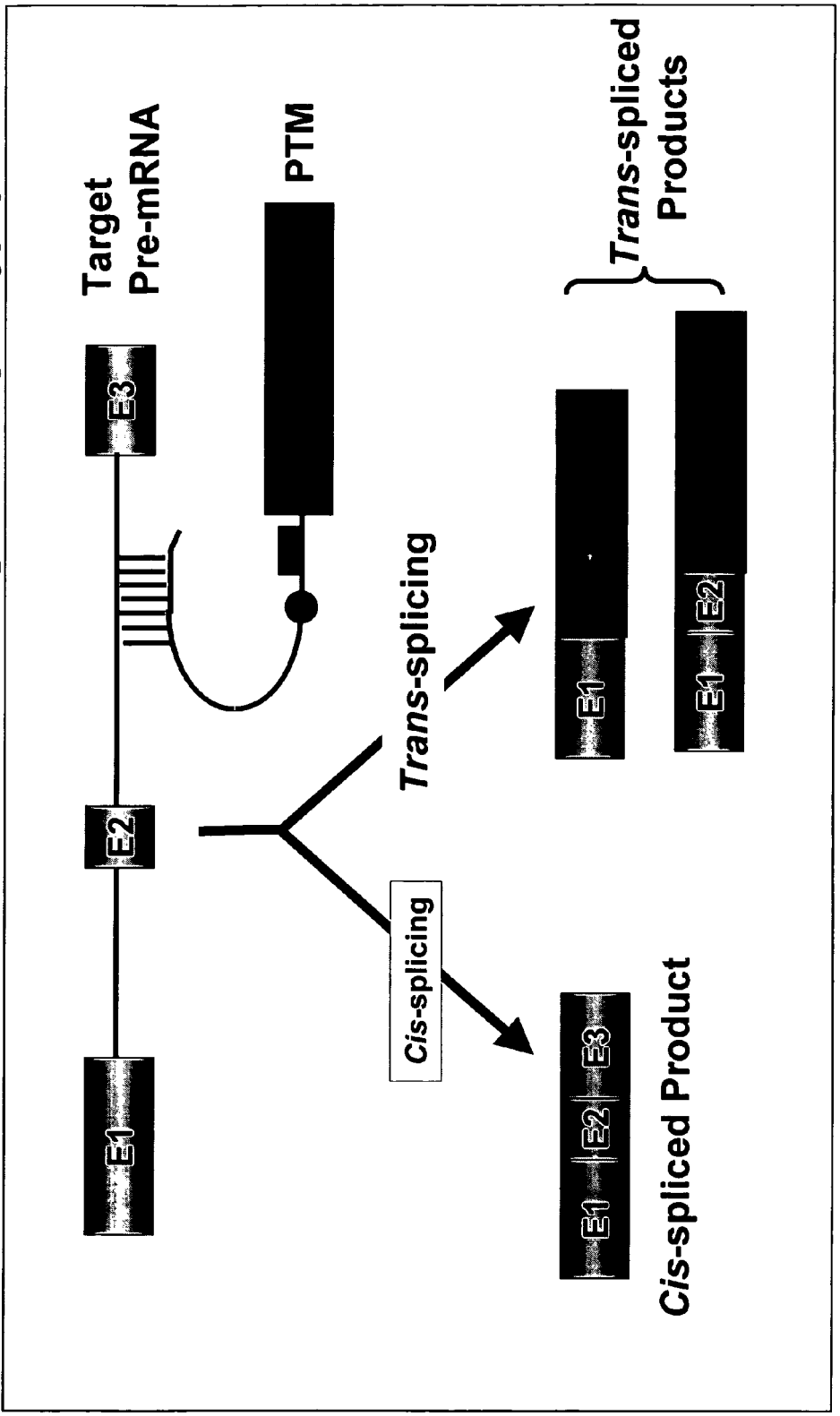
FIG. 4a shows a schematic representation of the splicing reactions between a target pre-mRNA and PTM comprising sequences encoding human immunoglobulin heavy chain.
Figure 4B:
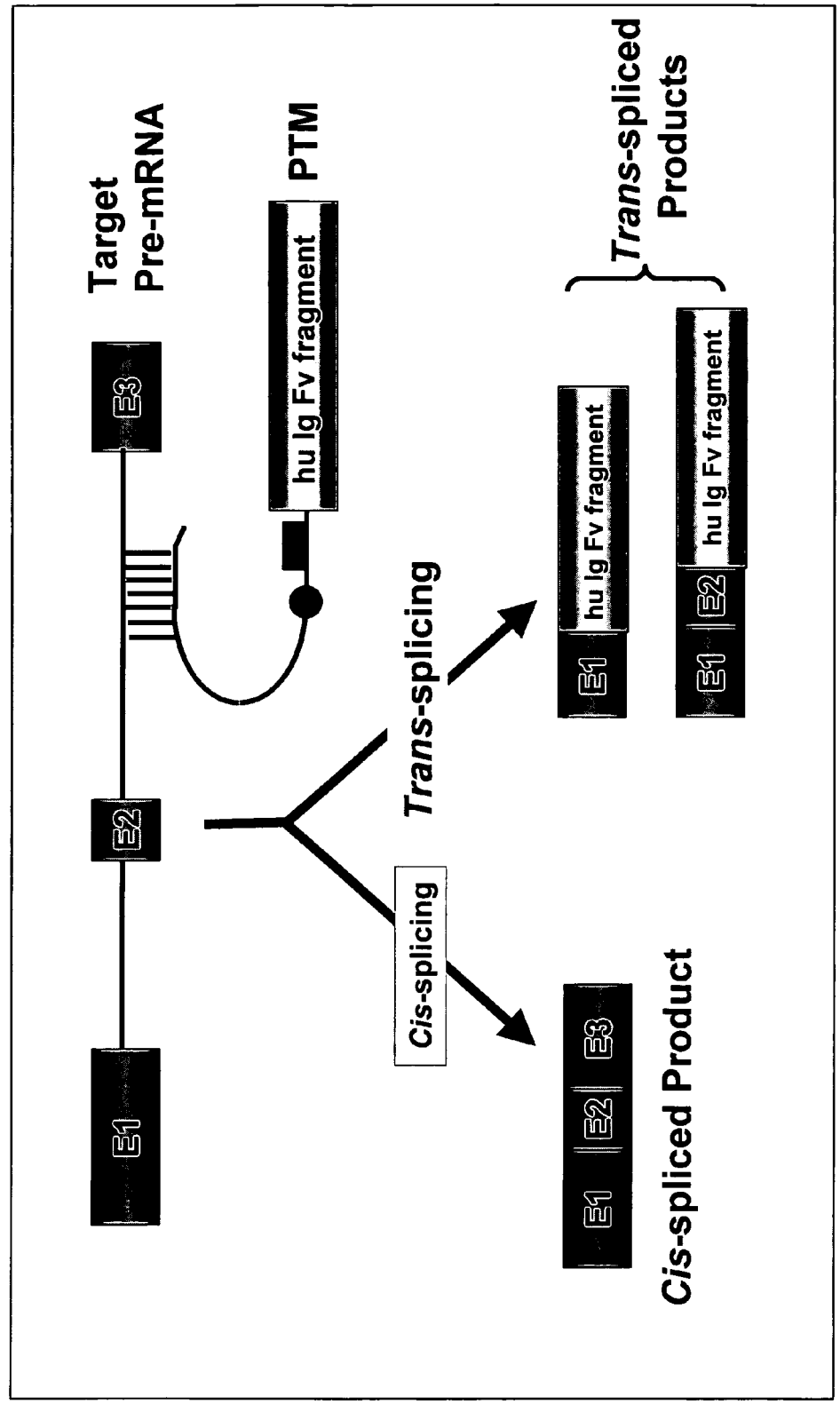
FIG. 4b shows a schematic representation of the splicing reactions between a target pre-mRNA and PTM comprising sequences encoding human Ig Fv fragment.
Figure 5:
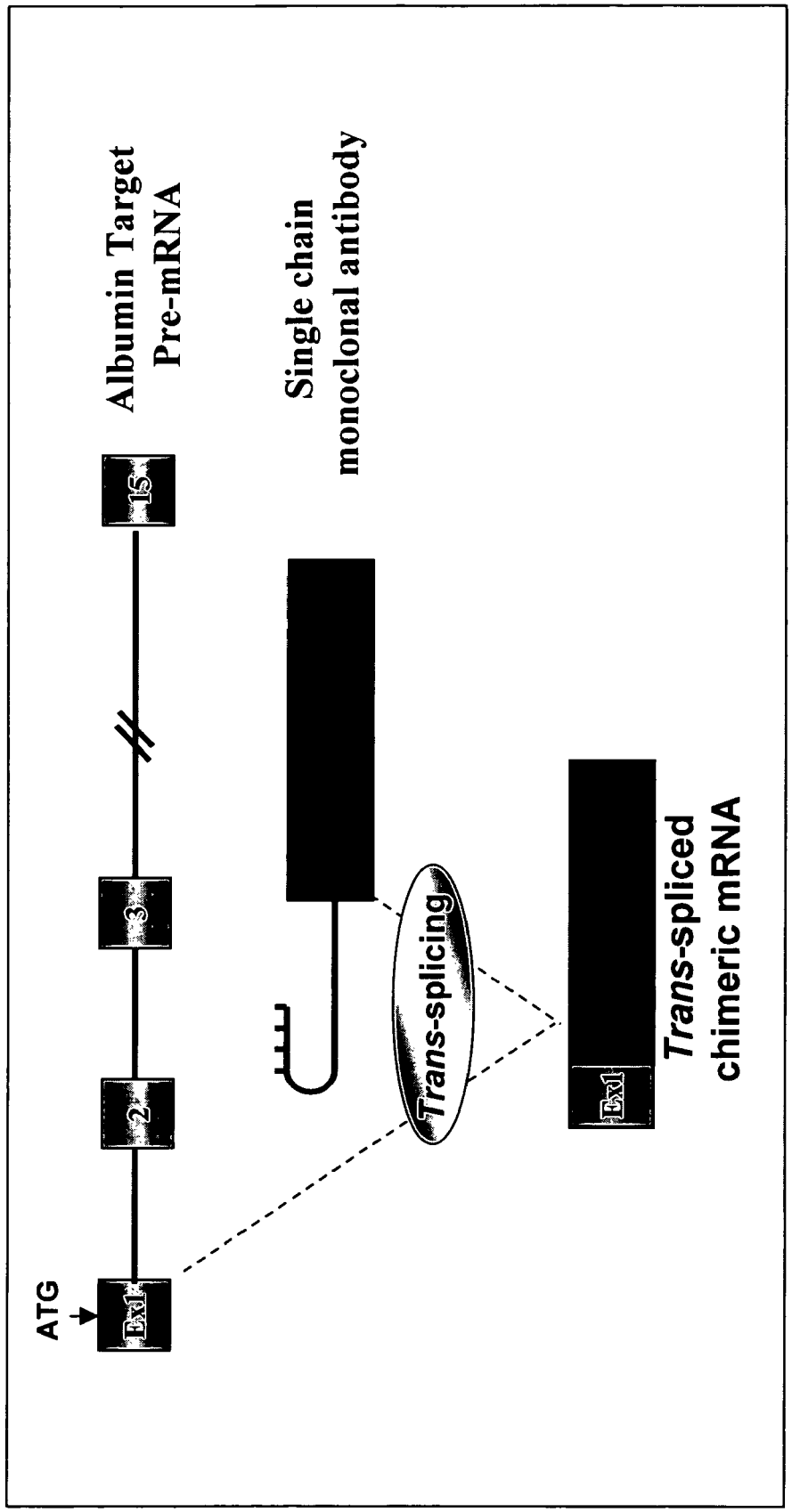
FIG. 5 shows a schematic representation of trans-splicing between an albumin pre-mRNA and PTM comprising sequences encoding a single chain monoclonal antibody.

The methods of the invention encompass contacting the PTMs of the invention with an abundantly expressed pre-mRNA target or a tumor specific or tumor associated pre-mRNA target, under conditions in which a portion of the PTM is trans-spliced to a portion of the abundantly expressed or tumor specific or associated pre-mRNA to form a novel chimeric RNA molecule comprising sequences encoding an antibody polypeptide. (See FIGS. 3, 4a and 4b)

As an abundantly expressed pre-mRNA, the RNA encoding albumin may be selected as the primary target, because it is a highly expressed pre-mRNA. However, other transcripts that are also expressed in high abundance could also be selected, such as, but not limited to, casein transcripts in breast tissue that are abundantly expressed in milk in humans and other animals. Other examples of abundantly expressed transcripts include those coding for myosin and fibroin.

Albumin pre-mRNA may be chosen, because serum concentration of albumin is sufficiently high, i.e. in the range of between 45-50 mg/ml. (See e.g., FIG. 6) Trans-splicing antibody sequences into albumin pre-mRNA will result in high concentrations of expressed antibody polypeptide molecules into the blood. Even a moderate 5% conversion of albumin pre-mRNA target will result in the production of significantly high antibody concentration, i.e., a physiologic or therapeutic concentration in the blood.

The nucleic acid molecules encoding the PTMs of the invention may be delivered to the primary target cell, namely hepatocytes, the major site of albumin production, followed by expression of the nucleic acid molecule to form a PTM capable of mediating a trans-splicing reaction. The target cell will vary depending on the abundantly expressed target, e.g. muscle cells and myosin transcripts.

In another embodiment of the invention, a tumor specific or tumor associated encoding transcript is selected as the target. Antigens that are exclusively or preferentially associated with cancer cells are deemed tumor specific antigens (TSA) or tumor associated antigens (TAA). These antigens include glycoproteins, lipoproteins and other types of macromolecules associated with certain types of cancers, such as human melanoma associated antigen, human neuroblastoma antigen, human breast cancer associated antigen, human ovary associated antigen, human sarcoma associated antigen, carcinoembryonic antigen, alphafetoprotein antigen or any other antigens associated with a malignant tumor (Rosenberg, Serologic Analysis of Human Cancer Antigens, Academic Press, New York, 1980.)

Specifically, the TAA may be a tumor specific antigen, such as an immunoglobulin idiotype (associated with non-Hodgkins' lymphoma), TCR (associated with T cell non-Hodgkin's lymphoma), mutant p21/ras (associated with pancreatic, colon and lung cancer), mutant p53 (associated with colorectal cancer, lung cancer, bladder cancer and head and neck cancer), p210/ber-ab1 fusion product (associated with chronic myelogenous leukemia and acute lymphoblastic leukemia). In addition, the TAA may be a developmental antigen, such as MART-1/melan A (associated with melanoma), MAGE-1 and MAGE-3 (associated with melanoma, colorectal cancer, lung cancer and gastric cancer), GAGE family (associated with melanoma and telomerase (associated with many cancers). The TAA may also be a viral antigen, such as those found on human papilloma virus (associated with cervical cancer and penile cancer), and Epstein Bar virus (associated with Burkitt's lymphoma, nasopharyngeal carcinoma and post-transplant lymphopoliferative disorders). The TAA may further be a tissue-specific self antigen, such as tyrosinase (associated with melanoma), gp 100 (associated with melanoma), prostatic acid phosphatase (associated with prostate cancer), prostatic-specific antigen (associated with prostate cancer), prostate-specific membrane antigen (associated with prostate cancer), thyroglobulin (associated with thyroid cancer) and alpha-fetoprotein (associated with liver cancer). Additionally, the TAA may be an over expressed self antigen, such as Her-2/neu (associated with breast cancer and lung cancer), carcinoembryonic antigen (associated with colorectal cancer, lung cancer and breast cancer), Muc-1 (associated with colorectal cancer, pancreatic cancer, ovarian cancer and lung cancer) and telomerase (associated with numerous tumors, see Nair et al., 2000, Nature Med. 6:1011-1017). Other examples of TAA include cyclin-dependent kinase 4 (melonoma cells), b-catenin (melanoma cells), and caspase-8 (squamous cell carcinoma cells). For a nonlimiting list of potential TAAs, see, e.g., Fong & Engleman, 2000, "Dendritic cells in cancer immunotherapy," Annu. Rev. Immunol. 18: 245-273.

In another embodiment of the invention, the PTMs may be contacted with viral or yeast infected cells containing a viral or yeast pre-mRNA target. For example, viral pre-mRNAs targeted using the PTMs of the present invention include, but are not limited to, those of Adenoviruses, Astroviruses, Filoviridae, Flaviviridae, Hepadnaviridae, Herpesviridae, Lentiviruses, Myoviridae, Norwalk Viruses, Orthomyxoviridae, Paramyxoviridae, Papovaviridae, Parvoviridae, Picornaviridae, Retroviridae and Rhabdoviruses.

The antibody encoded by the PTM may be directed against the product of the targeted pre-mRNA, i.e. the tumor specific or tumor associated antigen. In particular, the antibody produced as a result of trans-splicing would be directed against the protein encoded by the transcript targeted by the PTM in the same or separate cell.

Alternatively, the antibody encoded by the PTM could be directed against a separate protein produced by another pre-mRNA in this or another tumor cell. In particular, the PTM would target one tumor specific or tumor associated transcript, while the single chain antibody encoded by the PTM would be directed against a second tumor specific or tumor associated antigen. In both embodiments, the objective is to effect cell killing upon the binding of the antibody to its specific epitope.

Figure 6:
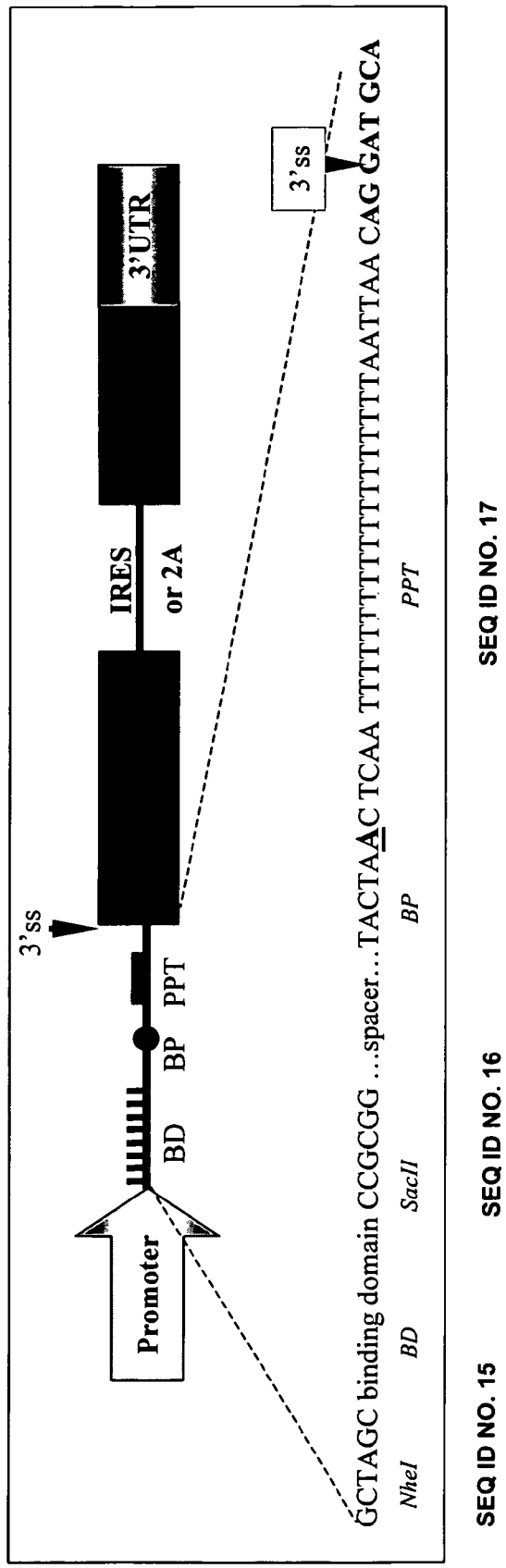
FIG. 6 shows a schematic representation of a bicistronic PTM for the production of whole antibodies, the PTM cassette consists of a trans-splice domain (TSD) including: binding domain, short spacer, BP, PPT, coding sequence for the entire light chain, 2A self-processing peptide from the foot and mouth disease virus (FMDV) or the encephlomayocarditties (ECMV) internal ribosome entry site (IRES) followed by the full length coding sequence of heavy chain. Abbreviations: BD, binding domain; BP, branch point; PPT, polypyrimidine tract; 3'ss, splice site.

In addition to the use of trans-splicing according to the present invention for the production of single chain antibodies, bicistronic PTMs can also be used according to the present invention. For example, bicistronic PTMs consisting of either a 2A self-processing oligo peptide derived from the foot and mouth disease virus (FMDV) (Fang et al., *Nature Biotechnol* 23: 584, 2005) or a internal ribosome entry site (IRES) (Martienz-Salas E, *Curr Opin Biotechnol*, 10: 458, 1999) can be used to simultaneously express the entire light and heavy chain. As illustrated in FIG. 6, the bicistronic PTMs are similar to a monocistronic PTM except that it contains either 2A FMDV self-processing oligo peptide or encephlomyocarditis (EMCV) IRES to induce high level expression of the heavy chain.

Structure of the Pre-Trans-Splicing Molecules

The present invention provides compositions for use in generating novel chimeric nucleic acid molecules through targeted trans-splicing. The PTMs of the invention comprise (i) one or more target binding domains that targets binding of the PTM to abundantly expressed pre-mRNA target (ii) a 3' splice region that includes a 3' splice acceptor site and/or 5' splice donor site; and (iii) nucleotide sequences encoding an antibody polypeptide. The antibody polypeptide could have a single chain structure or may be a variation, such as an intrabody or abzyme or sequences that confer additional function to the antibody. Alternatively the antibody polypeptide may be an F(ab), an H chain and/or a L chain.

The PTMs of the invention may also include at least one of the following features: (a) binding domains targeted to intron sequences in close proximity to the 3' or 5' splice signals of the target intron, (b) mini introns, and (c) ISAR (intronic splicing activator and repressor) consensus binding sites. The PTMs of the invention may further comprise one or more spacer regions to separate the RNA splice site from the target binding domain.

The general design, construction and genetic engineering of PTMs and demonstration of their ability to successful mediate spliceosome mediated trans-splicing reactions within the cell are described in detail in U.S. Pat. Nos. 6,083, 702, 6,013,487 and 6,280,978, as well as U.S. patent application Ser. Nos. 09/756,095, 09/756,096, 09/756,097, 09/838,858, 10/076,248 and 09/941,492, the disclosures of which are incorporated by reference in their entireties herein.

The target binding domain of the PTM endows the PTM with a binding affinity for the target pre-mRNA, e.g., albumin, casein or other target pre-mRNA. As used herein, a target binding domain is defined as any molecule, i.e., nucleotide, protein, chemical compound, etc., that confers specificity of binding and anchors the albumin pre-mRNA closely in space to the PTM so that the spliceosome processing machinery of the nucleus can trans-splice a portion of the PTM to a portion of the target pre-mRNA.

The target binding domain of the PTM may contain multiple binding domains that are complementary to and in antisense orientation to the targeted region of target pre-mRNA. The target binding domains may comprise up to several thousand nucleotides. In preferred embodiments of the invention, the binding domains may comprise at least 10 to 30 and up to several hundred or more nucleotides. The specificity of the PTM may be increased significantly by increasing the length of the target binding domain. For example, the target binding domain may comprise several hundred nucleotides or more. Absolute complementarily, although preferred, is not required. A sequence "complementary" to a portion of an RNA, as referred to herein, means a sequence having sufficient complementarity to be able to hybridize with the target pre-mRNA, forming a stable duplex. The ability to hybridize will depend on both the degree of complementarity and the length of the nucleic acid (See, for example, Sambrook et al., 1989, *Molecular Cloning, A Laboratory Manual*, 2d Ed., Cold Spring Harbor Laboratory Press, Cold Spring Harbor, N.Y.). Generally, the longer the hybridizing nucleic acid, the more base mismatches with an RNA it may contain and still form a stable duplex. One skilled in the art can ascertain a tolerable degree of mismatch or length of duplex by use of standard procedures to determine the stability of the hybridized complex.

Binding may also be achieved through other mechanisms, for example, through triple helix formation, aptamer interactions, antibody interactions or protein/nucleic acid interactions such as those in which the PTM is engineered to recognize a specific RNA binding protein, i.e., a protein bound to a specific target pre-mRNA.

The PTM molecule also contains a 3' splice region that includes a 3' splice acceptor AG site and/or a 5' splice donor site. The 3' splice region may further comprise a branchpoint and a polypyrimidine tract. Consensus sequences for the 5' splice donor site and the 3' splice region used in RNA splicing are well known in the art (See, Moore, et al., 1993, The RNA World, Cold Spring Harbor Laboratory Press, p. 303-358). In addition, modified consensus sequences that maintain the ability to function as 5' donor splice sites and 3' splice regions may be used in the practice of the invention. Briefly, the 5' splice site consensus sequence is AG/GURAGU (where A=adenosine, U=uracil, G=guanine, C=cytosine, R=purine and/=the splice site) (SEQ ID NO:1). The 3' splice site consists of three separate sequence elements: the branchpoint or branch site, a polypyrimidine tract and the 3' consensus sequence (YAG). The branch point consensus sequence in mammals is YNYURAC (Y=pyrimidine; N=any nucleotide) (SEQ ID NO:2). The underlined A is the site of branch formation. A polypyrimidine tract is located between the branch point and the splice site acceptor and is important for different branch point utilization and 3' splice site recognition. Recently, pre-mRNA introns beginning with the dinucleotide AU and ending with the dinucleotide AC have been identified and referred to as U12 introns. U12 intron sequences, as well as any sequences that function as splice acceptor/donor sequences, may also be used to generate the PTMs of the invention.

One or more spacer region(s) to separate the RNA splice site from the target binding domain may also be included in the PTM. The spacer region may be designed to include features such as (i) stop codons, which would function to block translation of any unspliced PTM and/or (ii) sequences that enhance trans-splicing to the target pre-mRNA.

A nucleotide sequence encoding an antibody polypeptide is also included in the PTM of the invention. The PTMs of the invention may contain exon sequences which when trans-spliced to the target pre-mRNA will result in the formation of a chimeric RNA capable of encoding a functional antibody polypeptide. The exon sequences may be derived from immunoglobulin genes, such as those encoding full length heavy chains, K light chain and X light chain. The exon sequences may encode Fab, Fv, or Fc fragments. Antibody polypeptides include single chain antibodies (SCA), i.e. antibodies that exist as a single polypeptide chain, and may comprise a heavy chain, light chain, and/or both. More preferably, the antibody polypeptides are single chain Fv antibodies in which a heavy chain variable region and a light chain variable region are joined together (directly or through a peptide linker) to form a continuous polypeptide. These single chain antibody polypeptides comprise an antigen binding portion and lack the antibody "constant" region, e.g., the Fc portion. The antigen binding portion folds into three dimensional structures substantially similar to the structure of the native full-length antibody and are known to those of skill in the art (see e.g., U.S. Pat. Nos. 5,091,513 and 5,132,405).

In another embodiment, the immunoglobulin molecule can be composed of smaller immunoglobulin forms such as (Fab)$_2$, Fab, sFv and CH$_2$-deleted domains enabling the antibodies to clear the blood stream at greater rates than intact immunoglobulin. Smaller immunoglobulin forms should have greater tumor to normal tissue ratios, which is an important element in cancer therapeutics.

It is preferred for human administration that all antibody polypeptide sequences be "humanized" to minimize the potential for an immune response to the polypeptide encoded by the PTM. To produce humanized antibodies, sequences from non-human immunoglobulin variable domain genes are substituted by the corresponding sequences from humans.

In another embodiment, the antibody molecule can be engineered to efficiently bind to a target, including targets that are relatively inaccessible, such as binding to a cleft or an enzyme active site. This can be accomplished by encoding the smallest functional unit of an antibody, such as that corresponding to the variable region of heavy (Hv) or light (Lv) chains of human antibodies. These configurations would enable two different targets to be engineered in a single molecule with dual targeting specificities to have two different therapeutic effects. Smaller antibodies would also improve tissue penetration, important in diseases such as cancer.

The nucleotide sequences encode antibody polypeptides directed to various disease targets, such as antigens associated with infection with pathogenic microorganisms, for example, viruses, such as HIV or hepatitis, bacteria, fungi and parasites may be included in the PTMs. Additionally, the PTM may include sequences encoding tumor-specific antibodies or antibodies directed to tumor-associated antigens such as, for example, Her2/Neu, CEA, MUC1, TRP-1, TRP-2 and MARTI/MelanA.

In addition, the encoded antibody polypeptides may also be directed to tissue-specific self-antigens. For example, known antigen or epitope mimicry between antigens on infectious organisms and self-antigens may be used to design antibody polypeptides and the PTMs encoding these polypeptides. In a specific embodiment of the invention, antibody polypeptides associated with autoimmune disease such as, for example, between the spirochete etiologic agent of Lyme disease and LFA-1 may be utilized to induce a protective immune response. Antibody polypeptides may also be directed to tissue-specific self-antigens associated with tumor antigens for use in cancer therapy.

Figure 7:
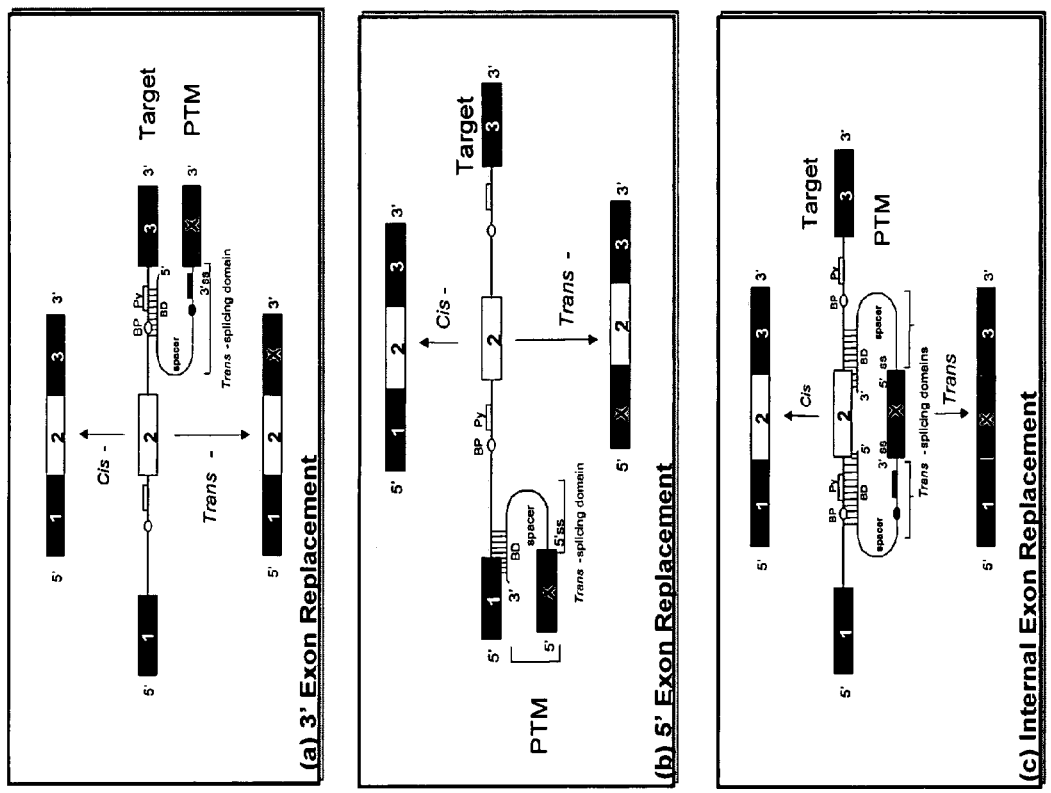
FIG. 7 shows a schematic representation of different trans-splicing reactions. (a) trans-splicing reactions between the target 5' splice site and PTM's 3' splice site, (b) trans-splicing reactions between the target 3' splice site and PTM's 5' splice site and (c) replacement of an internal exon by a double trans-splicing reaction in which the PTM carries both 3' and 5' splice sites. BD, binding domain; BP, branch point sequence; PPT, polypyrimidine tract; and ss, splice sites.

The PTM's of the invention may be engineered to contain a single exon sequence, multiple exon sequences, or alternatively the complete set of exon sequences encoding the antibody polypeptide of interest. The number and identity of the sequences to be used in the PTMs depends on the type of trans-splicing reaction, i.e., 5' exon replacement, 3' exon replacement or internal exon replacement that will occur (see FIG. 7).

In an embodiment of the invention, a "safety" is also incorporated into the spacer, binding domain, or elsewhere in the PTM to prevent non-specific trans-splicing. This is a region of the PTM that covers elements of the 3' and/or 5' splice site of the PTM by relatively weak complementarity, preventing non-specific trans-splicing. The PTM is designed in such a way that, upon hybridization of the binding/targeting portion(s) of the PTM, the 3' and/or 5'splice site is uncovered and becomes fully active.

Such "safety" sequences comprise one or more complementary stretches of cis-sequence (or could be a second, separate, strand of nucleic acid) which binds to one or both sides of the PTM branch point, pyrimidine tract, 3' splice site and/or 5' splice site (splicing elements), or could bind to parts of the splicing elements themselves. This "safety" binding prevents the splicing elements from being active (i.e. block U2 snRNP or other splicing factors from attaching to the PTM splice site recognition elements). The binding of the "safety" may be disrupted by the binding of the target binding region of the PTM to the target pre-mRNA, thus exposing and activating the PTM splicing elements.

A nucleotide sequence capable of forming a stem-loop structure may also be included in the PTM of the invention.

The present invention further provides PTM molecules wherein the coding region of the PTM is engineered to contain mini-introns. The insertion of mini-introns into the coding sequence of the PTM is designed to increase definition of the exon and enhance recognition of the PTM donor site. Mini-intron sequences to be inserted into the coding regions of the PTM include small naturally occurring introns or, alternatively, any intron sequences, including synthetic mini-introns, which include 5' consensus donor sites and 3' consensus sequences which include a branch point, a 3' splice site and in some instances a pyrimidine tract.

The mini-intron sequences are preferably between about 60-150 nucleotides in length, however, mini-intron sequences of increased lengths may also be used. In a preferred embodiment of the invention, the mini-intron comprises the 5' and 3' end of an endogenous intron. In preferred embodiments of the invention the 5' intron fragment is about 20 nucleotides in length and the 3' end is about 40 nucleotides in length.

In a specific embodiment of the invention, an intron of 528 nucleotides comprising the following sequences may be utilized. Sequence of the intron construct is as follows:

5' fragment sequence: (SEQ ID NO:3)

```
5' fragment sequence: (SEQ ID NO: 3)
Gtagttcttttgttcttcactattaagaacttaatttggtgtccatgtct cttttttttctagtttgtagtgctggaaggtattttggagaaattctt acatgagcattaggagaatgtatgggtgtagtgtcttgtataatagaaat tgttccactgataatttactctagttttttatttcctcatattattttca gtggcttttcttccacatctttatattttgcaccacattcaacactgta gcggccgc.
```

3' fragment sequence: (SEQ ID NO:4)

```
3' fragment sequence: (SEQ ID NO: 4)
Ccaactatctgaatcatgtgccccttctctgtgaacctctatcataatac
```

```
ttgtcacactgtattgtaattgtctcttttactttccccttgtatcttttg tgcatagcagagtacctgaaacaggaagtattttaaatattttgaatcaa atgagttaatagaatctttacaaataagaatatacacttctgcttaggat gataattggaggcaagtgaatcctgagcgtgatttgataatgacctaata atgatgggttttatttccag
```

In yet another specific embodiment of the invention, consensus ISAR sequences are included in the PTMs of the invention (Jones et al., NAR 29: 3557-3565). Proteins bind to the ISAR splicing activator and repressor consensus sequence, which includes a uridine-rich region that is required for 5' splice site recognition by U1 SnRNP. The 18 nucleotide ISAR consensus sequence comprises the following sequence: GGGCUGAUUUUUCCAUGU (SEQ ID NO:5). When inserted into the PTMs of the invention, the ISAR consensus sequences are inserted into the structure of the PTM in close proximity to the 5' donor site of intron sequences. In an embodiment of the invention the ISAR sequences are inserted within 100 nucleotides from the 5' donor site. In a preferred embodiment of the invention, the ISAR sequences are inserted within 50 nucleotides from the 5' donor site. In a more preferred embodiment of the invention the ISAR sequences are inserted within 20 nucleotides of the 5' donor site.

The compositions of the invention further comprise PTMs that have been engineered to include cis-acting ribozyme sequences. The inclusion of such sequences is designed to reduce PTM translation in the absence of trans-splicing or to produce a PTM with a specific length or defined end(s). The ribozyme sequences that may be inserted into the PTMs include any sequences that are capable of mediating a cis-acting (self-cleaving) RNA splicing reaction. Such ribozymes include but are not limited to hammerhead, hairpin and hepatitis delta virus ribozymes (see, Chow et al. 1994, *J Biol Chem* 269: 25856-64).

In an embodiment of the invention, splicing enhancers such as, for example, sequences referred to as exonic splicing enhancers may also be included in the structure of the synthetic PTMs. Transacting splicing factors, namely the serine/arginine-rich (SR) proteins, have been shown to interact with such exonic splicing enhancers and modulate splicing (See, Tacke et al., 1999, *Curr. Opin. Cell Biol.* 11: 358-362; Tian et al., 2001, *J. Biological Chemistry* 276: 33833-33839; Fu, 1995, RNA 1: 663-680). Nuclear localization signals may also be included in the PTM molecule (Dingwell and Laskey, 1986, *Ann. Rev. Cell Biol.* 2: 367-390; Dingwell and Laskey, 1991, *Trends in Biochem. Sci.* 16: 478-481). Such nuclear localization signals can be used to enhance the transport of synthetic PTMs into the nucleus where trans-splicing occurs.

Additional features can be added to the PTM molecule, such as polyadenylation signals to modify RNA expression/stability, or 5' splice sequences to enhance splicing, additional binding regions, "safety"-self complementary regions, additional splice sites, or protective groups to modulate the stability of the molecule and prevent degradation. In addition, stop codons may be included in the PTM structure to prevent translation of unspliced PTMs. Further elements such as a 3' hairpin structure, circularized RNA, nucleotide base modification, or synthetic analogs can be incorporated into PTMs to promote or facilitate nuclear localization and spliceosomal incorporation, and intracellular stability.

In addition to the PTM molecules described above, which are designed for spliceosome-mediated trans-splicing reactions, nucleic acid molecules may also be designed for ribozyme-mediated (group I and group II) or tRNA endonuclease mediated trans-splicing reactions.

When specific PTMs are to be synthesized in vitro (synthetic PTMs), such PTMs can be modified at the base moiety, sugar moiety, or phosphate backbone, for example, to improve stability of the molecule, hybridization to the target mRNA, transport into the cell, etc. For example, modification of a PTM to reduce the overall charge can enhance the cellular uptake of the molecule. In addition modifications can be made to reduce susceptibility to nuclease or chemical degradation. The nucleic acid molecules may be synthesized in such a way as to be conjugated to another molecule such as a peptide (e.g., for targeting host cell receptors in vivo), or an agent facilitating transport across the cell membrane (see, e.g., Letsinger et al., 1989, *Proc. Natl. Acad. Sci. USA* 86: 6553-6556; Lemaitre et al., 1987, *Proc. Natl. Acad. Sci.* 84: 648-652; PCT Publication No. WO 88/09810, published Dec. 15, 1988) or the blood-brain barrier (see, e.g., PCT Publication No. WO 89/10134, published Apr. 25, 1988), hybridization-triggered cleavage agents (see, e.g., Krol et al., 1988, *BioTechniques* 6: 958-976) or intercalating agents (see, e.g., Zon, 1988, *Pharm. Res.* 5: 539-549). To this end, the nucleic acid molecules may be conjugated to another molecule, e.g., a peptide, hybridization triggered cross-linking agent, transport agent, hybridization-triggered cleavage agent, etc.

The PTM may also encode sequences for a given cytokine or factor, in addition to the sequences for the antibody polypeptide that would enhance the action of the encoded antibody. The antibody sequences could also be fused with sequences that encode for another biologically active molecule, such as a toxin.

Various other well-known modifications to the nucleic acid molecules can be introduced as a means of increasing intracellular stability and half-life. Such modifications include, but are not limited to, the addition of flanking sequences of ribonucleotides to the 5' and/or 3' ends of the molecule. In some circumstances where increased stability is desired, nucleic acids having modified internucleoside linkages such as 2'-0-methylation may be preferred. Nucleic acids containing modified internucleoside linkages may be synthesized using reagents and methods that are well known in the art (see, Uhlmann et al., 1990, *Chem. Rev.* 90: 543-584; Schneider et al., 1990, Tetrahedron Lett. 31: 335 and references cited therein).

The PTMs of the present invention are preferably modified in such a way as to increase their stability in the cells. Since RNA molecules are sensitive to cleavage by cellular ribonucleases, it may be preferable to use as the competitive inhibitor a chemically modified oligonucleotide (or combination of oligonucleotides) that mimics the action of the RNA binding sequence but is less sensitive to nuclease cleavage. In addition, the synthetic PTMs can be produced as nuclease resistant circular molecules with enhanced stability to prevent degradation by nucleases (Puttaraju et al., 1995, *Nucleic Acids Symposium Series No.* 33: 49-51; Puttaraju et al., 1993, *Nucleic Acid Research* 21: 4253-4258). Other modifications may also be required, for example to enhance binding, to enhance cellular uptake, to improve pharmacology or pharmacokinetics or to improve other pharmaceutically desirable characteristics.

Modifications, which may be made to the structure of the synthetic PTMs include but are not limited to backbone modifications such as use of:

(i) phosphorothioates (X or Y or W or Z=S or any combination of two or more with the remainder as O). e.g. Y=S (Stein, C. A., et al., 1988, *Nucleic Acids Res.*, 16: 3209-3221), X=S (Cosstick, R., et al., 1989, *Tetrahedron Letters,* 30, 4693-4696), Y and Z=S (Brill, W. K.-D., et al., 1989, *J. Amer. Chem. Soc.,* 111: 2321-2322); (ii) methylphosphonates (e.g. Z=methyl (Miller, P. S., et al., 1980, *J. Biol. Chem.,* 255: 9659-9665); (iii) phosphoramidates (Z=N-(alkyl)$_2$ e.g. alkyl methyl, ethyl, butyl) (Z=morpholine or piperazine) (Agrawal, S., et al., 1988, *Proc. Natl. Acad. Sci. USA* 85: 7079-7083) (X or W=NH) (Mag, M., et al., 1988, *Nucleic Acids Res.,* 16: 3525-3543); (iv) phosphotriesters (Z=O-alkyl e.g. methyl, ethyl, etc) (Miller, P. S., et al., 1982, *Biochemistry,* 21: 5468-5474); and (v) phosphorus-free linkages (e.g. carbamate, acetamidate, acetate) (Gait, M. J., et al., 1974, *J. Chem. Soc. Perkin I,* 1684-1686; Gait, M. J., et al., 1979, *J. Chem. Soc. Perkin I,* 1389-1394).

In addition, sugar modifications may be incorporated into the PTMs of the invention. Such modifications include the use of: (i) 2'-ribonucleosides (R=H); (ii) 2'-O-methylated nucleosides (R=OMe)) (Sproat, B. S., et al., 1989, *Nucleic Acids Res.,* 17: 3373-3386); and (iii) 2'-fluoro-2'-riboxynucleosides (R=F) (Krug, A., et al., 1989, *Nucleosides and Nucleotides,* 8: 1473-1483).

Further, base modifications that may be made to the PTMs, including but not limited to use of: (i) pyrimidine derivatives substituted in the 5-position (e.g. methyl, bromo, fluoro etc) or replacing a carbonyl group by an amino group (Piccirilli, J. A., et al., 1990, *Nature,* 343: 33-37); (ii) purine derivatives lacking specific nitrogen atoms (e.g. 7-deaza adenine, hypoxanthine) or functionalized in the 8-position (e.g. 8-azido adenine, 8-bromo adenine) (for a review see Jones, A. S., 1979, *Int. J. Biolog. Macromolecules,* 1: 194-207).

In addition, the PTMs may be covalently linked to reactive functional groups, such as: (i) psoralens (Miller, P. S., et al., 1988, *Nucleic Acids Res.*, Special Pub. No. 20, 113-114), phenanthrolines (Sun, J-S., et al., 1988, *Biochemistry,* 27: 6039-6045), mustards (Vlassov, V. V., et al., 1988, *Gene,* 72: 313-322) (irreversible cross-linking agents with or without the need for co-reagents); (ii) acridine (intercalating agents) (Helene, C., et al., 1985, *Biochimie,* 67: 777-783); (iii) thiol derivatives (reversible disulphide formation with proteins) (Connolly, B. A., and Newman, P. C., 1989, *Nucleic Acids Res.,* 17: 4957-4974); (iv) aldehydes (Schiffs base formation); (v) azido, bromo groups (UV cross-linking); or (vi) ellipticines (photolytic cross-linking) (Perrouault, L., et al., 1990, *Nature,* 344: 358-360).

In an embodiment of the invention, oligonucleotide mimetics in which the sugar and internucleoside linkage, i.e., the backbone of the nucleotide units, are replaced with novel groups. For example, one such oligonucleotide mimetic, which has been shown to bind with a higher affinity to DNA and RNA than natural oligonucleotides, is referred to as a peptide nucleic acid (PNA) (for review see, Uhlmann, E. 1998, *Biol. Chem.* 379: 1045-52). Thus, PNA may be incorporated into synthetic PTMs to increase their stability and/or binding affinity for the target pre-mRNA.

In another embodiment of the invention, the PTMs may be covalently linked to lipophilic groups or other reagents capable of improving uptake by cells. For example, the PTM molecules may be covalently linked to: (i) cholesterol (Letsinger, R. L., et al., 1989, *Proc. Natl. Acad. Sci. USA,* 86: 6553-6556); (ii) polyamines (Lemaitre, M., et al., 1987, *Proc. Natl. Acad. Sci, USA,* 84: 648-652); other soluble polymers (e.g. polyethylene glycol) to improve the efficiently with which the PTMs are delivered to a cell. In addition, combinations of the above identified modifications may be utilized to increase the stability and delivery of PTMs into the target cell. The PTMs of the invention can be used in methods designed to produce a novel chimeric RNA in a target cell.

The methods of the present invention comprise delivering to the target cell a PTM which may be in any form used by one skilled in the art, for example, an RNA molecule, or a DNA vector which is transcribed into a RNA molecule, wherein said PTM binds to a target pre-mRNA target and mediates a trans-splicing reaction resulting in formation of a chimeric mRNA that expresses an antibody polypeptide.

Synthesis of the Trans-Splicing Molecules

The nucleic acid molecules of the invention can be RNA or DNA or derivatives or modified versions thereof, single-stranded or double-stranded. By nucleic acid is meant a PTM molecule, a ribozyme or t-RNA endonuclease based nucleic acid molecule, or a nucleic acid molecule encoding a PTM molecule, a ribozyme or t-RNA endonuclease based nucleic acid molecule, whether composed of deoxyribonucleotides or ribonucleosides, and whether composed of phosphodiester linkages or modified linkages. The term nucleic acid also specifically includes nucleic acids composed of bases other than the five biologically occurring bases (adenine, guanine, thymine, cytosine and uracil). In addition, the PTMs of the invention may comprise, DNA/RNA, RNA/protein or DNA/RNA/protein chimeric molecules that are designed to enhance the stability of the PTMs.

The PTMs of the invention can be prepared by any method known in the art for the synthesis of nucleic acid molecules. For example, the nucleic acids may be chemically synthesized using commercially available reagents and synthesizers by methods that are well known in the art (see, e.g., Gait, 1985, *Oligonucleotide Synthesis: A Practical Approach,* IRL Press, Oxford, England).

Alternatively, synthetic PTMs can be generated by in vitro transcription of DNA sequences encoding the PTM of interest. Such DNA sequences can be incorporated into a wide variety of vectors downstream from suitable RNA polymerase promoters such as the T7, SP6, or T3 polymerase promoters. Consensus RNA polymerase promoter sequences include the following:

```
T7:   TAATACGACTCACTATAGGGAGA     (SEQ ID NO: 6)

SP6:  ATTTAGGTGACACTATAGAAGNG     (SEQ ID NO: 7)

T3:   AATTAACCCTCACTAAAGGGAGA.    (SEQ ID NO: 8)
```

The base in bold is the first base incorporated into RNA during transcription. The underline indicates the minimum sequence required for efficient transcription.

RNAs may be produced in high yield via in vitro transcription using plasmids, such as SPS65 and Bluescript (Promega Corporation, Madison, Wis.). In addition, RNA amplification methods such as Q-β amplification can be utilized to produce the PTM of interest.

The PTMs may be purified by any suitable means, as are well known in the art. For example, the PTMs can be purified by gel filtration, affinity or antibody interactions, reverse phase chromatography or gel electrophoresis. Of course, the skilled artisan will recognize that the method of purification will depend in part on the size, charge and shape of the nucleic acid to be purified.

The PTMs of the invention, whether synthesized chemically, in vitro, or in vivo, can be synthesized in the presence of modified or substituted nucleotides to increase stability, uptake or binding of the PTM to target pre-mRNA. In addition, following synthesis of the PTM, the PTMs may be modified with peptides, chemical agents, antibodies, or nucleic acid molecules, for example, to enhance the physical properties of the PTM molecules. Such modifications are well known to those of skill in the art.

In instances where a nucleic acid molecule encoding a PTM is utilized, cloning techniques known in the art may be used for cloning of the nucleic acid molecule into an expression vector. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

The DNA encoding the PTM of interest may be recombinantly engineered into a variety of host vector systems that also provide for replication of the DNA in large scale and contain the necessary elements for directing the transcription of the PTM. The use of such a construct to transfect target cells in the patient will result in the transcription of sufficient amounts of PTMs that will form complementary base pairs with the endogenously expressed pre-mRNA targets, and thereby facilitate a trans-splicing reaction between the complexed nucleic acid molecules. For example, a vector can be introduced in vivo such that is taken up by a cell and directs the transcription of the PTM molecule. Such a vector can remain episomal or become chromosomally integrated, as long as it can be transcribed to produce the desired RNA, i.e., PTM. Such vectors can be constructed by recombinant DNA technology methods standard in the art.

Vectors containing the PTM of interest can be any plasmid, viral, including non-viral synthetic delivery systems or others known in the art, used for replication and expression of nucleic acids in mammalian cells. Expression of the sequence encoding the PTM can be regulated by any promoter/enhancer sequences known in the art to act in mammalian, preferably human cells. Such promoters/enhancers can be inducible or constitutive. Such promoters include but are not limited to: the SV40 early promoter region (Benoist, C. and Chambon, P. 1981, *Nature* 290: 304-310), the promoter contained in the 3' long terminal repeat of Rous sarcoma virus (Yamamoto et al., 1980, *Cell* 22: 787-797), the herpes thymidine kinase promoter (Wagner et al., 1981, *Proc. Natl. Acad. Sci. U.S.A.* 78: 14411445), the regulatory sequences of the metallothionein gene (Brinster et al., 1982, *Nature* 296: 39-42), the viral CMV promoter, the human chorionic gonadotropin-β promoter (Hollenberg et al., 1994, *Mol. Cell. Endocrinology* 106: 111-119), etc.

Any type of plasmid, cosmid, YAC or viral vector can be used to prepare the recombinant DNA construct, which can be introduced directly into the tissue site. Alternatively, viral vectors can be used which selectively infect the desired target cell. Vectors for use in the practice of the invention include any eukaryotic expression vectors, including but not limited to, viral expression vectors, such as those derived from the class of retroviruses, adenoviruses or adeno-associated viruses.

The PTMs can also be delivered as RNA molecules directly.

A number of selection systems can also be used, including but not limited to selection for expression of the herpes simplex virus thymidine kinase, hypoxanthine-guanine phosphoribosyltransferase and adenine phosphoribosyl transferase protein in tk-, hgprt- or aprt-deficient cells, respectively. Also, anti-metabolic resistance can be used as the basis of selection for dihydrofolate reductase (dhfr), which confers resistance to methotrexate; xanthine-guanine phosphoribosyl transferase (gpt), which confers resistance to mycophenolic acid; neomycin (neo), which confers resistance to aminoglycoside G-418; and hygromycin B phosphotransferase (hygro), which confers resistance to hygromycin. In a preferred embodiment of the invention, the cell culture is transformed at a low ratio of vector to cell, such that there will be only a single vector, or a limited number of vectors, present in any one cell.

Uses and Administration of Trans-Splicing Molecules

The compositions and methods of the present invention are designed to generate novel chimeric RNA molecules containing sequences that express an antibody polypeptide. Specifically, targeted spliceosome mediated trans-splicing, including double-trans-splicing reactions, 3' exon replacement and/or 5' exon replacement can be used to generate such chimeric RNAs. Additionally, ribozyme or t-RNA mediated targeted trans-splicing reactions may be utilized to form chimeric RNAs.

Various delivery systems are known and can be used to transfer the compositions of the invention into cells, e.g. encapsulation in liposomes, microparticles, microcapsules, recombinant cells capable of expressing the composition, receptor-mediated endocytosis (see, e.g., Wu and Wu, 1987, *J. Biol. Chem.* 262: 4429-4432), construction of a nucleic acid as part of a retroviral, adenoviral, adeno-associated viral, lentiviral or other vector, naked DNA injection, electroporation, calcium phosphate mediated transfection, etc.

PTM and the delivery system would constitute the product, which could be administered to animals or humans by conventional administration methods, such as intravenous or intraportal injection. In a specific embodiment of the invention, the chimeric RNA molecule would be distributed throughout the circulation, but would be active in liver cells that express the albumin pre-mRNA target. The PTM would be active in its RNA form, the binding domain of the PTM adhering to the targeted sequence in albumin pre-mRNA. Following trans-splicing, the coding domain of the PTM that contains sequences of the specific antibody would be inserted or trans-spliced to a defined sequence of the albumin target, resulting in a chimeric mRNA that would express a product comprising the antibody polypeptide, which can be secreted from the hepatocytes. Secretory signaling sequences could be incorporated to increase secretion.

The albumin gene is highly expressed in the liver, thereby providing an abundant target pre-mRNA for targeting. By targeting albumin, the serum concentration of the product is expressed at physiologically significant, clinical and/or therapeutic levels. Albumin has a serum concentration on the order of 45-50 mg/ml. Given a moderate trans-splicing efficiency of 5%, large quantities of product can be produced in vivo. Based on a plasma concentration of 45 mg/ml of albumin and an even more moderate trans-splicing efficiency of 1%, 2.5 mg/ml of the product may be generated. The product, which comprises the antibody or polypeptide fragment, is generally present approximately at a concentration of 500 µg/ml in the serum of the subject, which is significantly above a desired therapeutic amount. In humans, the therapeutic antibody levels may be in the range of 3-30 µg/ml of serum. If the achieved levels of antibodies are too high, the administrated dose can be decreased to reduce the serum concentration.

Tumor-specific antigens, infectious disease agents and biodefense agents (e.g., anthrax, flu, smallpox, SARS, lupas rheumatoid arthritis and cancer) are potential targets for the diagnosis and treatment of patients and could have important functions as signal transducing receptors or cell adhesion molecules in tumorigenesis and normal development. The compositions of the present invention may be used to target cancer cells specifically using tumor-specific antigens. The PTMs can be engineered to effect cell-specific cell killing upon binding of the antibody to the tumor-specific antigen.

The compositions and methods of the present invention may also be used to confer immunity in a host. Specifically, targeted trans-splicing, including double-trans-splicing reactions, 3' exon replacement and/or 5' exon replacement can be used to form a chimeric RNA between a target pre-RNA and the PTM wherein said chimeric RNA encodes a fusion protein comprising the antibody polypeptide of interest.

The compositions and methods can be used to provide a nucleic acid encoding an antibody polypeptide to cells of an individual where expression of said polypeptide causes induction of a protective immune response. Specifically, the compositions and methods can be used to provide sequences encoding an antibody polypeptide of interest capable of enhancing immunity to cells of an individual to induce a protective immune response, such as GM-CSF, for example.

As used herein, the phrase "induction of a protective immune response", and the like, is used broadly to include the induction of any immune-based response in a host, natural or artificial, including either an antibody or cell-mediated immune response, or both, that serves to protect the host against the particular pathogen or cancer cell. Induction of a protective immune response also includes the induction of an autoimmune response against tissue-specific self antigens (Pardoll, D. M. 1999, PNAS 96: 5340-5342). The term refers not only to the absolute prevention of any of the symptoms or conditions in the host resulting from infection with the particular pathogen, or from the cancer, but also to any detectable delay in the onset of any such symptoms or conditions, any detectable reduction in the degree or rate of infection by the particular pathogen, or any detectable reduction in the severity of the disease or any symptom or condition resulting from the presence of cancer cells. Compositions according to the present invention, which comprise the antibody polypeptide of interest, should be administered at a dosage and for a duration sufficient to reduce one or more clinical signs associated with the infection of the host.

The compositions and methods can be used to alleviate and/or treat various diseases and disorders. For example, PTMs may be administered to a subject to treat and/or ameliorate an other infectious disease, caused by, for example, HIV, RSV, hepatitis A, B or C, Class II or IV agents or any microorganism. In addition, PTMs may be administered to a subject having cancer, autoimmune diseases, rheumatoid arthritis and transplantation. Treatment includes amelioration of any symptom associated with the disease or clinical indication associated with the pathology.

Additionally, cells comprising the PTMs of the invention may be further engineered to express cytokine/growth factors that can facilitate the recruitment of immunologic cells to the cell comprising the PTM. Such cytokine/growth factors are well know to those of skill in the art and include, for example, granulocyte/macrophage stimulating cell growth factor (GMCSF), interleukins or similarly acting molecules. In certain embodiments, the PTM may encode both an antibody polypeptide and a cytokinel growth factor.

In a preferred embodiment, nucleic acids comprising a sequence encoding a PTM are administered to promote PTM function, by way of gene delivery and expression into a host cell. In this embodiment of the invention, the nucleic acid mediates an effect by promoting PTM production. Any of the methods for gene delivery into a host cell available in the art can be used according to the present invention. For general reviews of the methods of gene delivery see Strauss, M. and Barranger, J. A., 1997, Concepts in Gene Therapy, by Walter de Gruyter & Co., Berlin; Goldspiel et al., 1993, *Clinical Pharmacy* 12: 488-505; Wu and Wu, 1991, *Biotherapy* 3: 87-95; Tolstoshev, 1993, *Ann. Rev. Pharmacol. Toxicol.* 33: 573-596; Mulligan, 1993, *Science* 260: 926-932; and Morgan and Anderson, 1993, *Ann. Rev. Biochem.* 62: 191-217; 1993, TIBTECH 11(5): 155-215. Exemplary methods are described below.

Delivery of the PTM into a host cell may be either direct, in which case the host is directly exposed to the PTM or PTM encoding nucleic acid molecule, or indirect, in which case, host cells are first transformed with the PTM or PTM encoding nucleic acid molecule in vitro, then transplanted into the host. These two approaches are known, respectively, as in vivo or ex vivo gene delivery.

In a specific embodiment, the nucleic acid is directly administered in vivo, where it is expressed to produce the PTM. This can be accomplished by any of numerous methods known in the art, e.g., by constructing it as part of an appropriate nucleic acid expression vector and administering it so that it becomes intracellular, e.g. by infection using a defective or attenuated retroviral or other viral vector (see e.g., U.S. Pat. No. 4,980,286), or by direct injection of naked DNA, or by use of microparticle bombardment (e.g., a gene gun; Biolistic, Dupont, Bio-Rad), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, *J. Biol. Chem.* 262: 4429-4432).

In a specific embodiment, a viral vector that contains the PTM can be used. For example, a retroviral vector can be utilized that has been modified to delete retroviral sequences that are not necessary for packaging of the viral genome and integration into host cell DNA (see Miller et al., 1993, *Meth. Enzymol.* 217: 581-599). Alternatively, adenoviral or adeno-associated viral vectors can be used for gene delivery to cells or tissues. (See, Kozarsky and Wilson, 1993, *Current Opinion in Genetics and Development* 3: 499-503 for a review of adenovirus-based gene delivery).

In a preferred embodiment of the invention, an adeno-associated viral vector may be used to deliver nucleic acid molecules capable of encoding the PTM. The vector is designed so that, depending on the level of expression desired, the promoter and/or enhancer element of choice may be inserted into the vector.

Another approach to gene delivery into a cell involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. The resulting recombinant cells can be delivered to a host by various methods known in the art. In a preferred embodiment, the cell used for gene delivery is autologous to the host's cell.

The present invention also provides for compositions comprising an effective amount of a PTM or a nucleic acid encoding a PTM, and a physiologically or pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable carriers are described in "Remington's Pharmaceutical sciences" by E. W. Martin.

Many methods standard in the art can be thus employed, including but not limited to hybridization assays to detect formation of chimeric mRNA expression by detecting and/or visualizing the presence of chimeric mRNA (e.g., Northern assays, dot blots, in situ hybridization, and Reverse-Transcription PCR, etc.), etc.

In a specific embodiment, it may be desirable to administer the pharmaceutical compositions of the invention locally to the area in need of treatment, i.e., liver tissue or tumor tissue. This may be achieved by, for example, and not by way of limitation, local infusion during surgery, topical application, e.g., in conjunction with a wound dressing after surgery, by injection, by means of a catheter, by means of an endoscope, by means of a suppository, or by means of an implant, said implant being of a porous, non-porous, or gelatinous material, including membranes, such as sialastic membranes, or fibers. Other control release drug delivery systems, such as nanoparticles, matrices such as controlled-release polymers, hydrogels.

The PTM will be administered in amounts that are effective to produce the desired effect in the targeted cell. Effective dosages of the PTMs can be determined through procedures well known to those in the art that address such parameters as biological half-life, bioavailability and toxicity. The amount of the composition of the invention which will be effective will depend on the severity of the disease/pathology being treated, and can be determined by standard clinical techniques. Such techniques include analysis of samples to determine if the level of target protein expression has been reduced. In addition, in vitro assays may optionally be employed to help identify optimal dosage ranges.

The following examples are meant to exemplify the present invention and as such are not intended or to be interpreted as limiting the scope of the invention.

Example 1

Figure 8:
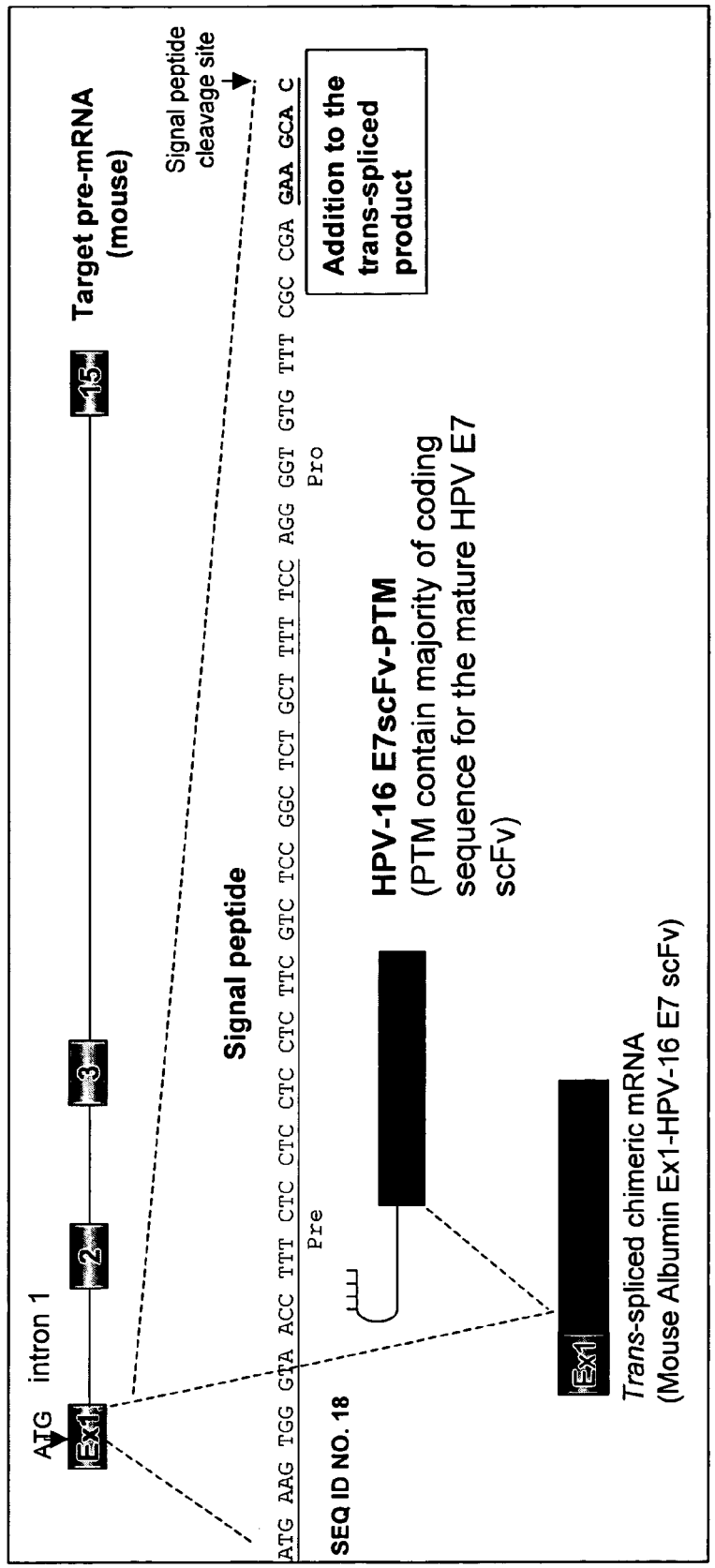
FIG. 8 shows the present invention applied to trans-splicing mediated HPV-16 E7 single chain antibody production strategy.

In Vivo Trans-Spliced Albumin-HPV-16 Anti-E7 Single Chain Antibody (mALB-HPV-16 Anti-E7 SCFV) cDNA The albumin targeting strategy shown in FIG. 8 has been evaluated for the production of human papilloma virus type 16 (HPV-16) anti-E7 single chain antibody in vivo. The concept involves targeted trans-splicing of HPV-16 anti-E7 scFv sequence into albumin pre-mRNA target. Albumin has been selected as a target because of its elevated expression in the liver to provide high albumin pre-mRNA concentration for abundant trans-splicing targets. The present study evaluated the effect of albumin sequences on expression, secretion and function of HPV-16 anti-E7 scFv in vivo.

Figure 9:
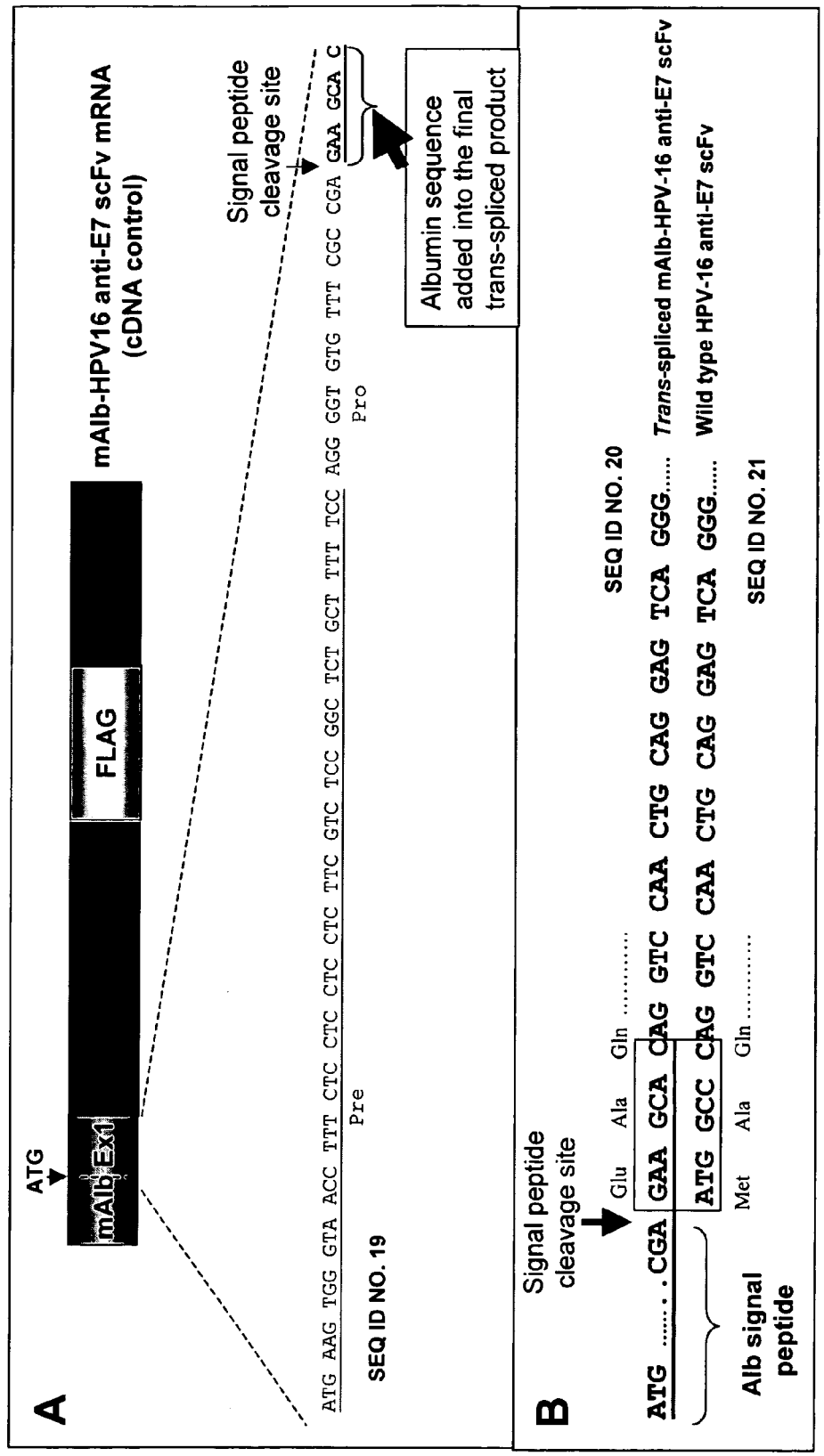
FIG. 9a shows a schematic illustration of mouse albumin exon I-HPV16 anti-E7 scFv cDNA.
FIG. 9b shows trans-spliced mAlb-HPV-16 anti-E7 scFv having the signal peptide cleavage site of Albumin.

The mouse albumin-HPV-16 anti-E7 scFv (mAlb-HPV16 anti-E7 scFv) positive control cDNA (FIG. 9) was constructed to imitate the final trans-spliced product and tested for expression, processing and secretion in Cos-7 and Hepal-6 (mouse hepatoma cells) cells. The trans-spliced cDNA expression plasmid was constructed using long synthetic complementary oligonucleotides and PCR product consisting of coding albumin exon 1 and HPV-16 anti-E7 scFv sequence. The coding sequence of mouse albumin exon 1 was assembled using the following long oligonucleotides: forward primer (SEQ ID NO:9): GCTAGC ATGAAGTGGGTAACCTTTCTCCTCCTCCTCTTCGTCT CCGGCTCTGCTTTTTCCAGGGGTGT-GTTTCGCCGAGAAGCACAGGTCCAACTG-CAGGAGTCAGGGGCTGAGC, and reverse primer (SEQ ID NO:10): GCTCAGCCCCTGACTCCTGCAGTTG-GACCTGTGCTTCTCGGCGAAACACACCCCTGG AAAAAGCAGAGCCGGAGACGAAGAGGAG-GAGGAGAAAGGTTACCCACTTCATGCTAGC. (The nucleotides in bold include NheI and BlpI restriction sites used for cloning; underlined nucleotides include the mouse albumin exon 1 sequence, in which the majority codes for signal peptide; and the italicized nucleotides include partial HPV-16 anti-E7 scFv sequence).

HPV-16 anti-E7 scFv coding sequence was PCR amplified using a cDNA clone and primers: ScaI (5'-GCTAGCATGGC-CCAGGTCCAACTGCAGG) (SEQ ID NO:11) and Sca5 (5'-AAGCTT TCA CTTGTCGTCATCGTCTTTGTAGTC CCGTTTTATTTCC GCTTG GTCCCAGC) (SEQ ID NO: 12) (nucleotides in bold, NheI and Hind III restriction sites for cloning; italicized nucleotides, stop codon; and the underlined nucleotides, FLAG tag). The PCR product was digested with BlpI and HindIII restriction enzymes. The resulting product was first ligated with the annealed oligo fragment and then ligated into pcDNA3.1 expression vector (Invitrogen). The authenticity of the PTM cassette sequence was verified by sequencing (FIG. 10).

Example 2

Production Expression and Secretion of Alubumin-HPV-16 Anti-E7 SCFV Antibody in HEPA1-6 and COS-7 Cells The effect of the albumin exon 1 sequence (7 nucleotides) on expression and processing of HPV-16 anti-E7 scFv was evaluated by transfecting the trans-spliced cDNA plasmid along with a control plasmid (similar to the trans-spliced cDNA without the FLAG tag) into mouse hepatoma, Hepal-6 and Cos-7 cells. 48 hrs post-transfection, medium was collected, passed through FLAG affinity column (Sigma, Cat# FLAGIPT-1) and analyzed by Western blot for the expression of HPV-16 anti-E7 scFv using anti-FLAG M2 monoclonal antibody (Sigma, Cat# F 3165).

Figure 11:
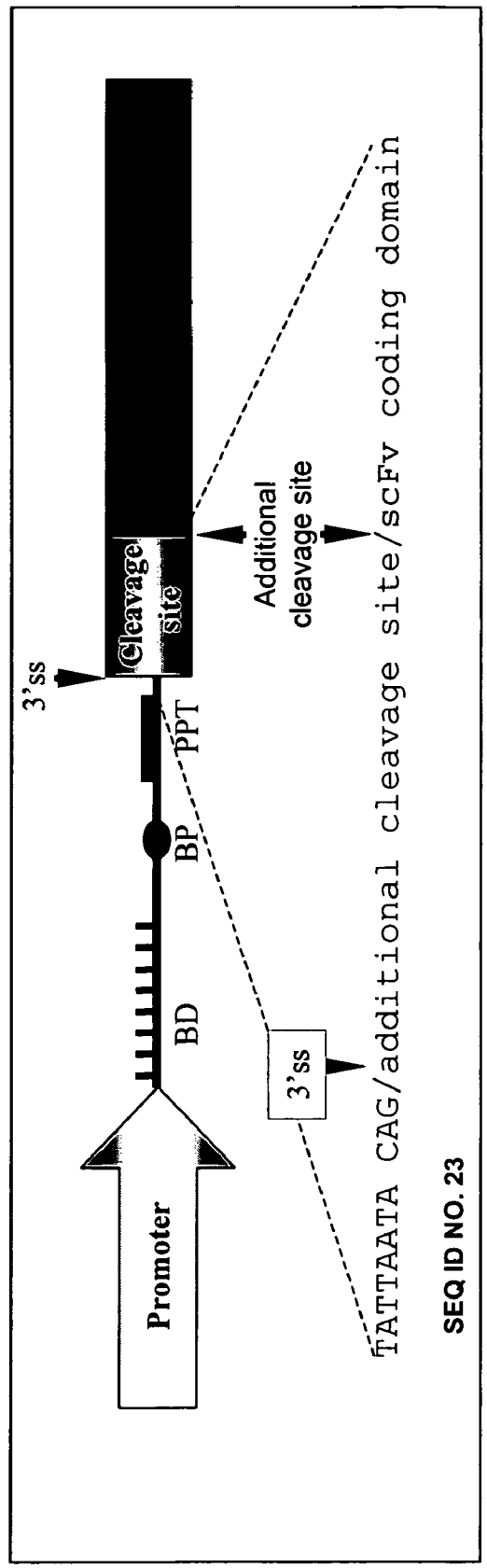
FIG. 11 shows a schematic illustration of PTM containing additional endopeptidase cleavage site. The PTM structure is similar to scFv PTM except that it has an additional endopeptidase cleavage site or a native "Pro"-peptide sequence.
Figure 12:
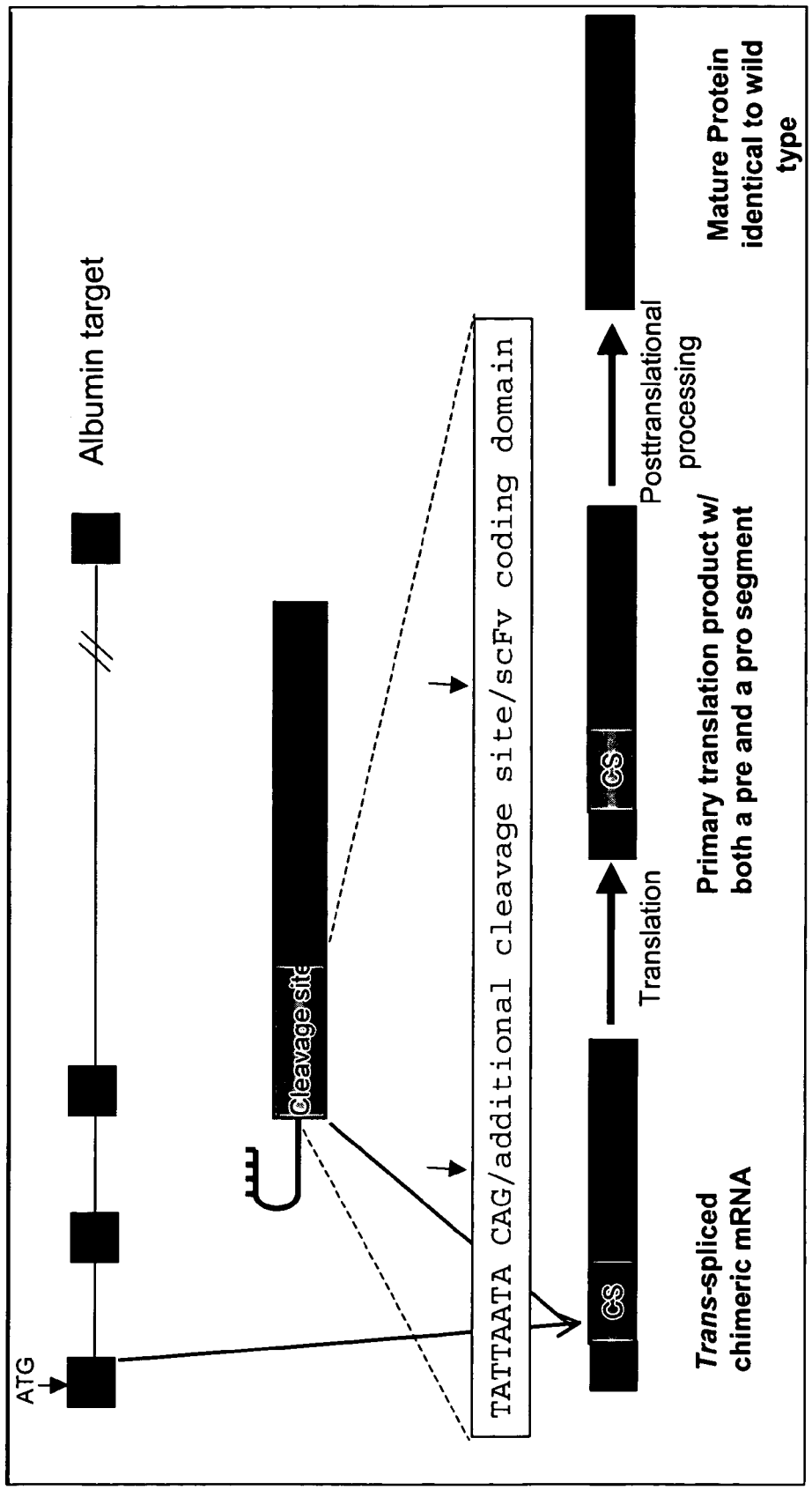
FIG. 12 shows a schematic illustration of trans-splicing strategy to eliminate albumin sequence in the final product. Ex1, exon 1 of albumin; CS, additional cleavage site.

The albumin trans-splicing strategy results in the production of chimeric mRNA and protein. The final trans-spliced product contains 7 nucleotides or 2 amino acids from albumin target mRNA. For human applications it may be desirable to eliminate the albumin sequence in the final product to preclude immunological reactions. In one exemplary strategy, illustrated in FIG. 11, the PTM is engineered to encode "Furin" like endopeptidase (or proprotein convertase) cleavage site which has been used to express proteins in vivo (Fuller R S, Brake A J, Thorner J, *Science,* 246: 482-486, 1989; Bresnahan P A, Leduc R, Thomas L, Thorner J, Gibson H L, Brake A J, Barr P J, Thomas G., *J Cell Biol.* 111: 2851-2859, 1990; van de Ven W J, Voorberg J, Fontijn R, Pannekoek H, van den Ouweland A M, van Duijnhoven H L, Roebroek A J, Siezen R J, *Mol Biol Rep.* 14: 265-75, 1990; Duckert P, Brunak S, Blom N. *Protein Eng Design & Selection.* 17: 107-112, 2004). In another example, the PTM can be designed to include the protein's own native secretion signal, i.e., "pre-pro" signal (if it has one). This strategy is designed to take advantage of the endogenous native cellular machinery to enhance recognition, processing and secretion of the final trans-spliced protein to the site of action similar to wild type protein. For example, trans-splicing of PTM into albumin pre-mRNA target produces a chimeric mRNA and prepro-protein that, in addition to signal peptide cleavage in rough endoplasmic reticulum, undergoes several post-translational modifications in other cellular compartments and, finally, endopeptidase cleavage resulting in the release of a mature, fully processed biologically active protein that is identical to the wild type (FIG. 12).

Figure 13:
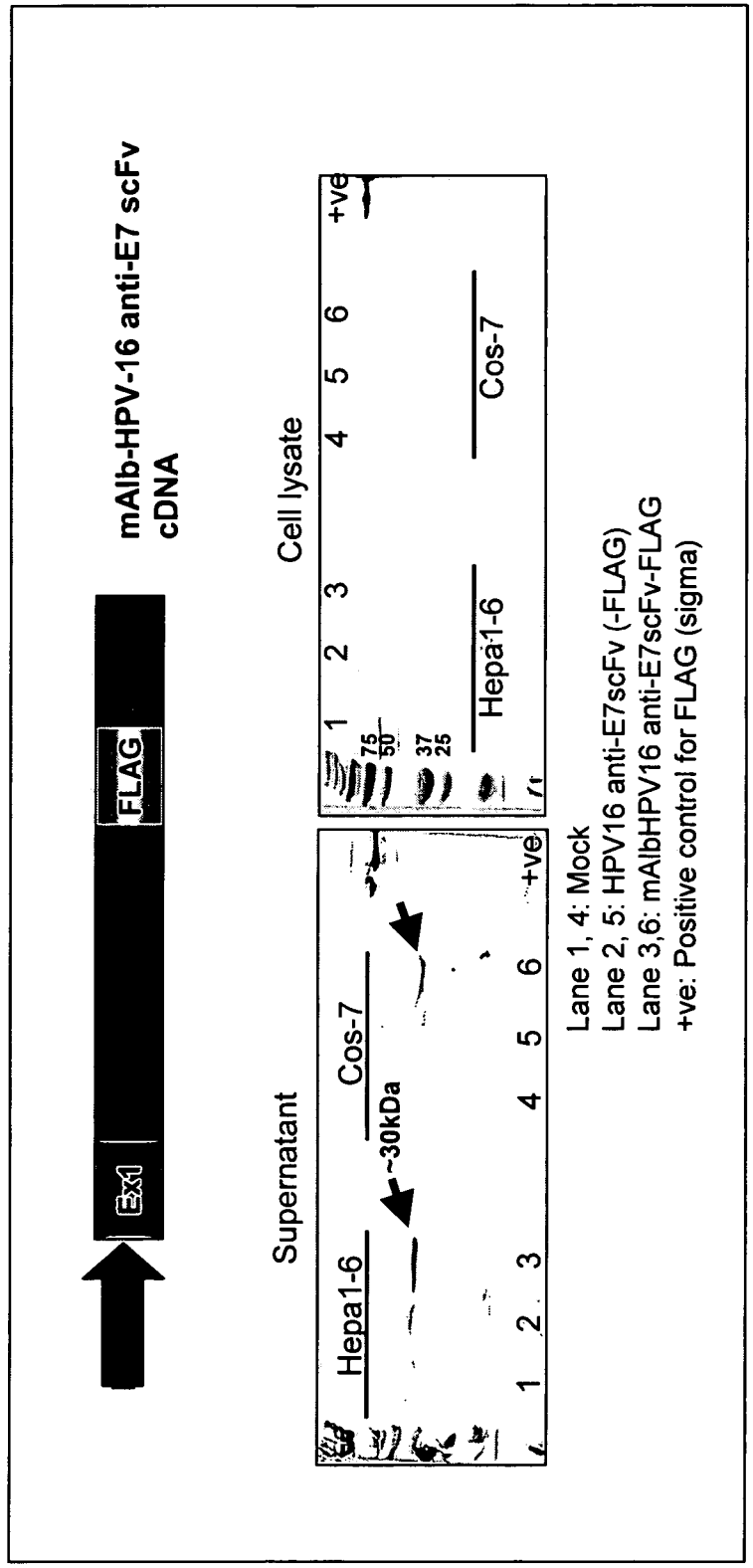
FIG. 13 shows a SDS gel showing the production of HPV16 anti-E7 scFv in Hepal-6 cells. Mouse albumin-HPV16 anti-E7 scFv cDNA (identical to the trans-spliced mRNA) was transfected into Hepal-6 and Cos-7 cells. 48 hrs post-transfection, supernatant and cell lysate was prepared and analyzed by Western blot using anti-FLAG M2 monoclonal antibody. Arrows indicate the expected ~30 kDa mouse albumin-HPV16 anti-E7 scFv.

About 10 μg of total protein from the supernatant or the total cell lysate from cells transfected with cDNA expression plasmids was analyzed on a 12% SDS-PAGE and transferred onto nylon membrane and probed with anti-FLAG antibody. Western results confirmed the production of HPV-16 anti-E7 scFv, 30 kDa in size predicted for the mature protein in cells that were transfected with FLAG-tagged cDNA expression plasmid in both Hepa1-6 and Cos-7 cells (FIG. 13 lanes 3 & 6, left panel). On the other hand, no such product was detected in mock and in cells that received the cDNA construct without the FLAG tag (FIG. 13 lanes 1-2 and 5-6, left panel). In addition, no protein was detected in the cell lysate (FIG. 13) indicating that the majority of the protein was processed and secreted normally.

Example 3

Trans-Spliced Albumin HPV-16 Anti-E7 SCFV Protein is Functionally Active

The effect of the albumin sequence on HPV-16 anti-E7 scFv function was evaluated by its ability to down regulate HPV-16 E7 expression in cervical cancer cells. Cervical cancer cells, SiHa, (ATCC # HTB-35) that are HPV-16 E7 oncoprotein positive were transfected with mAlb-HPV-16 anti-E7 scFv cDNA expression plasmid. The matching control cells, C-33A (ATCC # HTB-31) that do not express E7 oncoprotein were also transfected with the mAlb-HPV-16 anti-E7 scFv cDNA expression plasmid. Cells were grown for 5 days and the number of relative viable cells was determined by colorimetric (MTT) assay.

Figure 14:
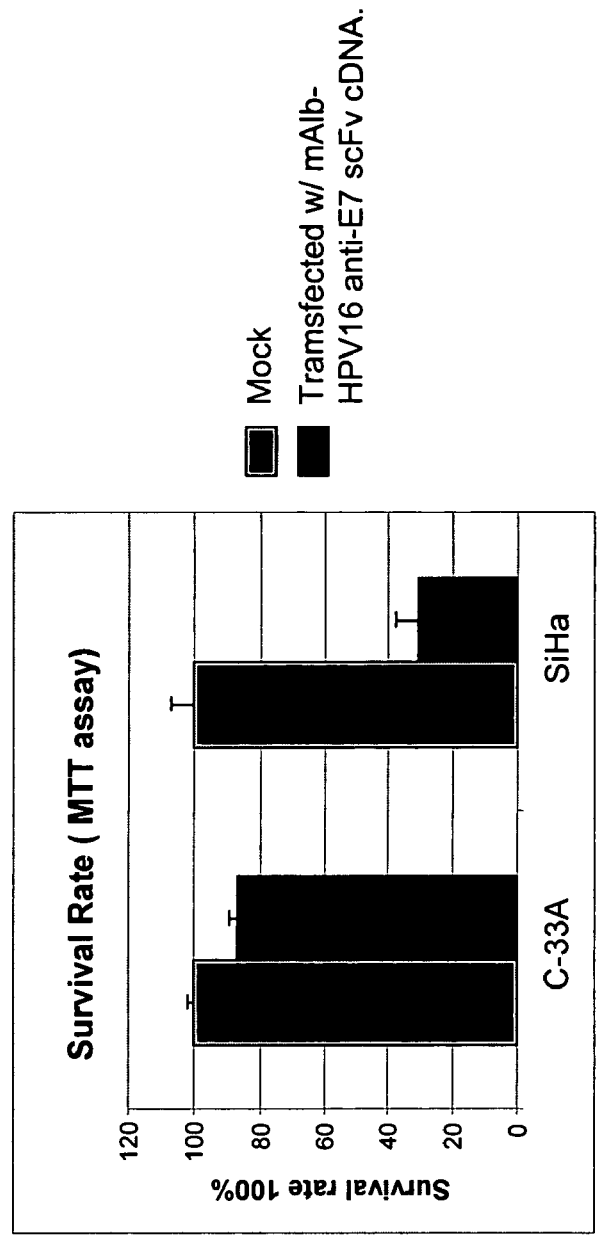
FIG. 14 shows the trans-spliced mAlb-HPV16 anti-E7 scFv function in cells. HPV-positive cervical cancer cells, SiHa, or the matching HPV-negative cells were transfected with mAlb-HPV16 anti-E7 scFv expression cDNA plasmid. Cells were grown for 5 days and assayed for cell survival using MTT assay.

In the case of HPV-16 positive cervical cancer cells, SiHa, mAlb-HPV-16 anti-E7 scFv inhibited cell proliferation by ~75% compared to about <10% inhibition in C-33A HPV-negative cells, thereby demonstrating the functionality of the trans-spliced albumin HPV-16 anti-E7 scFv antibody (FIG. 14). These results not only confirmed the absence of any major adverse effects due to albumin sequence in the final trans-spliced product on HPV-16 anti-E7 scFv function, but also provide evidence of the effectiveness of the compositions of the present invention for the production of functional antibody polypeptides and/or therapeutic proteins in vivo.

Figure 15:
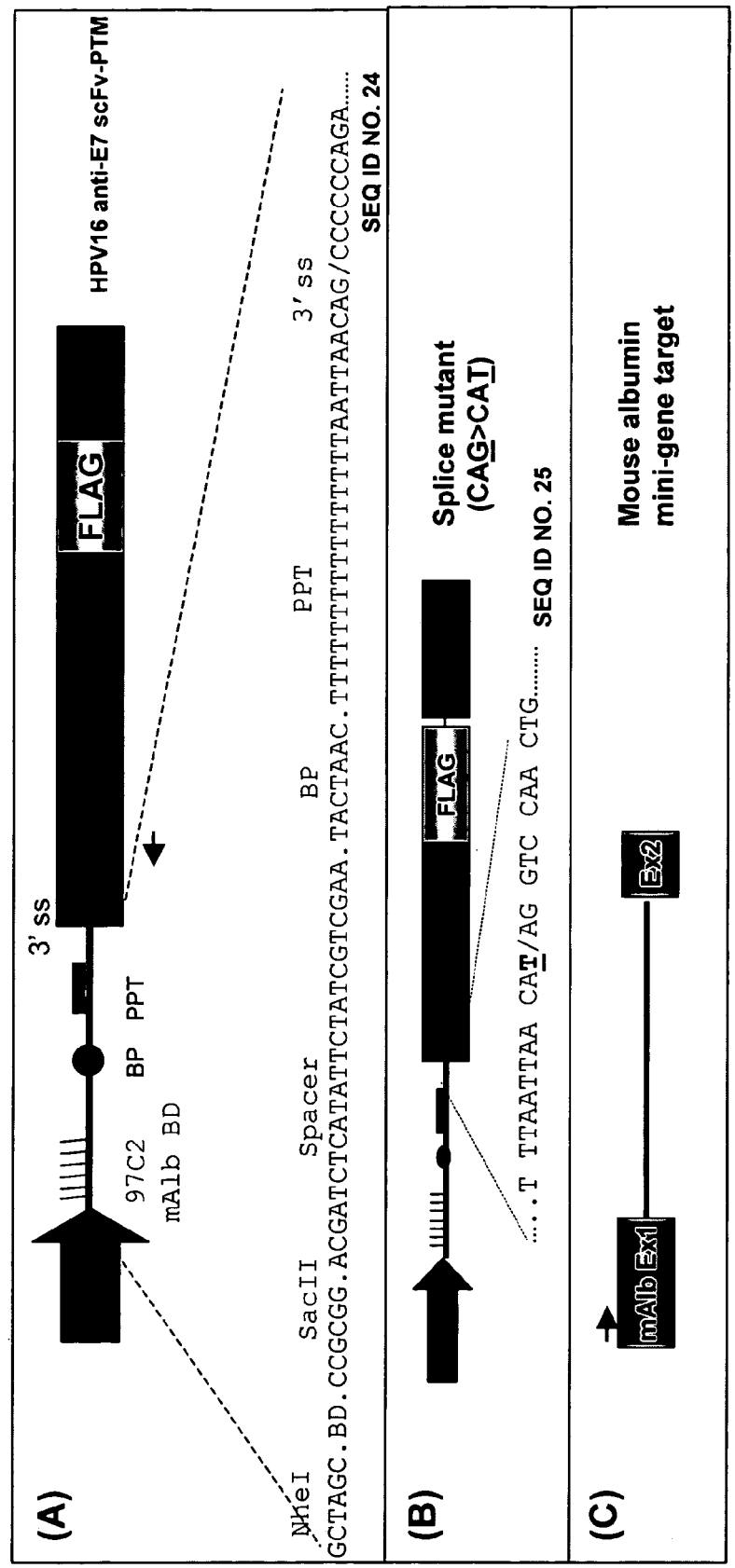
FIG. 15 shows a schematic of HPV16 anti-E7 scFv PTM (A), splice mutant (B) and mouse albumin mini-gene target (C), used for in vitro POP studies. PTM cassette consists of a trans-splicing domain which includes mouse albumin intron 1 specific binding domain (BD), short spacer, consensus sequence branch point (BP), optimized polypyrimidne tract (PPT), 3' acceptor site (CAG) followed by the majority of the coding sequence of HPV16 anti-E7 scFv sequence. PTM Expression is driven by CMV promoter. At the 3' end, the PTM also it contains FLAG epitope followed by bovine growth hormone polyadenylation signal (BGH pA). Splice mutant is identical to the functional PTM but has a point mutation at the acceptor site (CA<u>G</u>>CA<u>T</u>). ss, 3' splice site; arrows indicate primers used for trans-splicing assays.

The structure of HPV-16 anti-E7 scFv PTM expression cassette used for this study is illustrated in FIG. 15A. The PTM cassette consists of a trans-splicing domain (TSD) that includes 279 nts binding domain complementary to mouse albumin intron 1, 24 nucleotide spacer region, strong 3' splice elements such as the consensus yeast branch point (BP), an optimized polypyrimidine tract, a splice acceptor site (CAG dinucleotide) followed by the majority of the coding sequence for HPV-16 anti-E7 scFv (FIG. 13). The PTM cassette also contains a bovine growth hormone polyadenylation signal and FLAG tag to assist in the detection of trans-spliced protein. The entire cassette was cloned into the pcDNA3.1 vector backbone, which contains the cytomegalovirus (CMV) promoter (Invitrogen). In addition, the vector backbone was further modified to include the Maz4 (transcriptional pause site) sequence to reduce cryptic cis-splicing between vector ampicillin gene and the PTM 3' splice site.

A splice mutant (splice incompetent) was also constructed that was identical to the functional PTM described above but had a point mutation at the acceptor site (CA$\underline{G}$>CA$\underline{T}$) (FIGS. 15A and 15B). The splice mutant was used as a negative control. For in vitro proof-of-principle studies, a mouse albumin mini-gene target pre-mRNA was used that consisted of exon 1, intron 1 and exon 2. A schematic diagram of the pre-mRNA target is illustrated in FIG. 15C.

Figure 16:
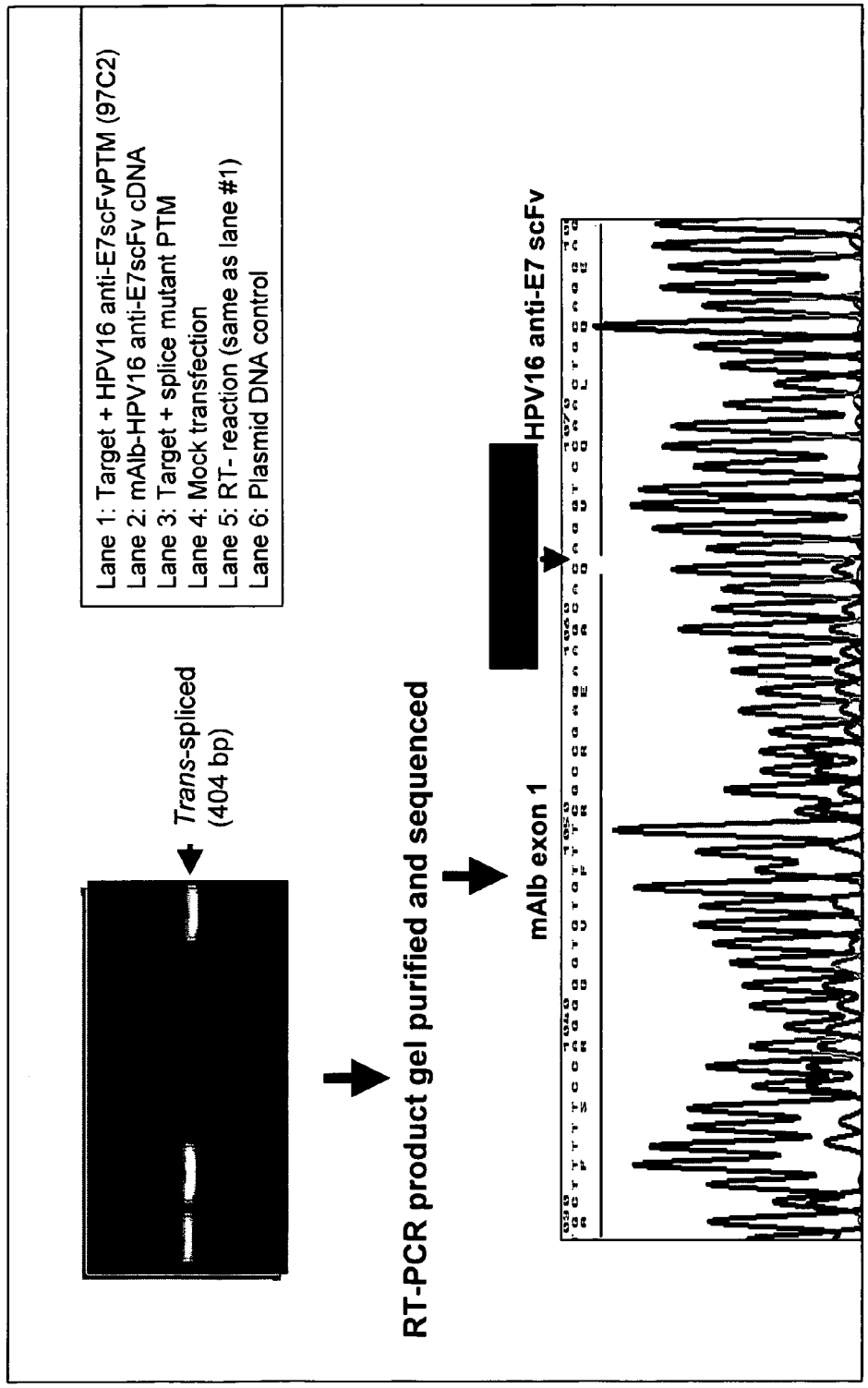
FIG. 16 shows the precise trans-splicing of HPV16 anti-E7 scFv PTM into mouse albumin exon 1 in cells.

PTM mediated trans-splicing and production of mouse albumin-HPV-16 anti-E7 scFv chimeric mRNA was evaluated by co-transfecting Hepa1-6 cells with mouse albumin mini-gene target plasmid along with HPV-16 anti-E7 scFv PTM (functional PTM) or with the splice mutant (splice incompetent PTM) and mock transfection. Total RNA isolated from these cells was analyzed by RT-PCR using mouse albumin exon 1 (AlbA1TSF2: ACCTTTCTCCTCCTC-CTCTTCGT) (SEQ ID NO:13) and HPV-16 anti-E7 scFv PTM (sca3: AGTAAGCAAACCAGTAGCCGTC) (SEQ ID NO:14) specific primers (primer binding sites indicated in FIGS. 15A and 15C). These primers produced the predicted 404 bp product only in cells that received both target and functional PTM (FIG. 16, lane 1) which co-migrated along with a similar size band observed with cDNA control (FIG. 16, lane 2) and plasmid DNA (FIG. 16, lane 6). No RT-PCR product was detected in cells transfected with the splice mutant (FIG. 16, lane 3) or in mock transfection (FIG. 16, lane 4). The PCR product was purified and was directly sequenced, confirming the precise trans-splicing to the predicted splice sites of the PTM and the target pre-mRNA in these cells (FIG. 16, lower panel). Thus, the above results establish that the methods of the present invention may be used to provide efficient trans-splicing of HPV-16 anti-E7 scFv PTM in vitro.

Example 4

In Vivo Trans-Splicing to Endogenous Mouse Albumin Pre-mRNA Target and Production of HPV-16 Anti-E7 SCFV in Mice To demonstrate trans-splicing of the PTM into an endogenous mouse albumin target and production of HPV-16 anti-E7 scFv protein, the following experiments were conducted. One hundred micrograms of mAlb-HPV16 anti-E797C2 (PTM only), 70 μg of PTM+35 μg of mini-gene target (additional target plasmid to increase pre-mRNA concentration) or 100 μg of the control cDNA (mAlb-HPV16 anti-E7scFv) plasmid that mimics trans-spliced mRNA were hydrodynamically injected via tail vein into normal C57Bl/6 mice. Serum samples were collected at 8, 16 and 24 hrs time points and analyzed by Western blot. Approximately, 25-100 μl serum was passed through FLAG affinity column, samples were then separated on a 12% SDS-PAGE, transferred on to nitrocellulose membrane and probed with anti-FLAG M2 monoclonal antibody. Proteins were visualized using a chemiluminescence kit (Invitrogen, Cat# WB7103).

Figure 17A:
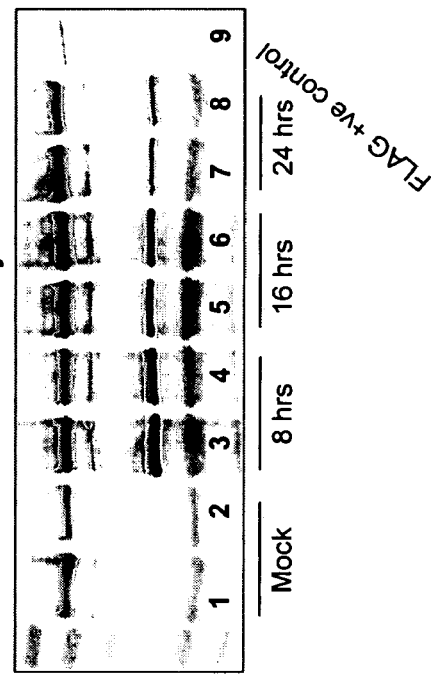
FIG. 17A shows Western blot analysis of serum samples from mice injected with mAlb-HPV16 anti-E7 scFv cDNA. 25 µl serum was passed through FLAG affinity column and analyzed by Western blot using anti-FLAG M2 monoclonal antibody.
Figure 17B:
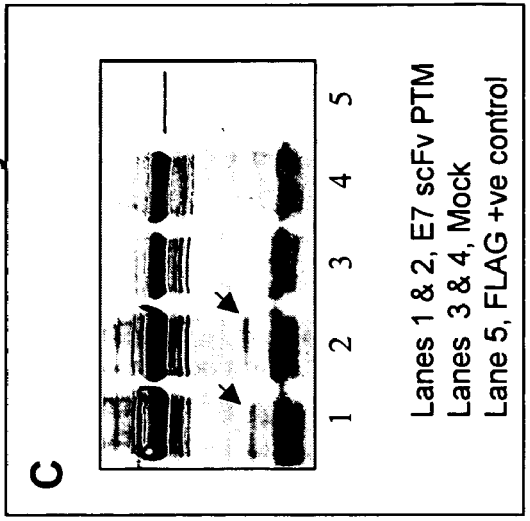
FIG. 17B shows Western blot analysis of serum from mice injected with HPV16 anti-E7 scFv PTM only. 50-100 μl serum was passed through FLAG affinity column and analyzed by Western blot using anti-FLAG M2 monoclonal antibody.
Figure 17C:
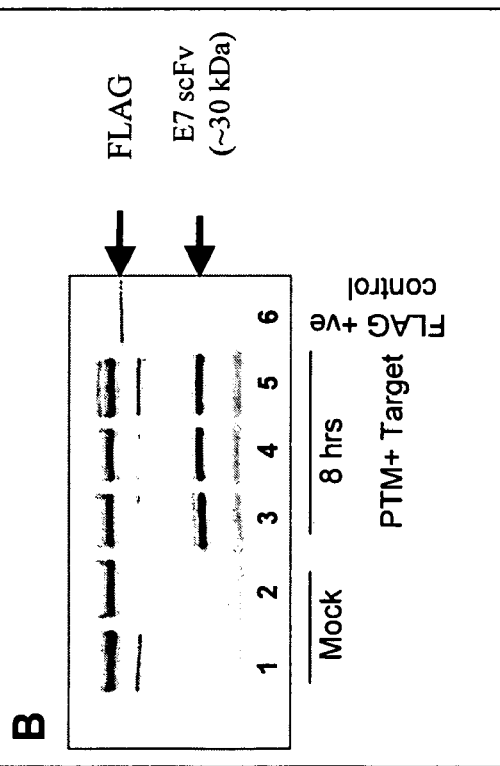
FIG. 17C shows Western blot analysis of serum from mice injected with HPV16 anti-E7 scFv PTM+target. 50-100 μl serum was passed through FLAG affinity column and analyzed by Western blot using anti-FLAG M2 monoclonal antibody.

Western blot results indicated the appearance of HPV-16 anti-E7 scFv in the circulation of the mice as early as 8 hrs post-injection with the cDNA control expression plasmid (FIG. 17A, lanes 3 and 4) and the levels dropped significantly at 24 hrs (FIG. 17A, lanes 7 and 8). Efficient trans-splicing and production of predicted 30 kDa HPV16 anti-E7 scFv was also detected in mice that received both the target and PTM (FIG. 17B, lanes 3-5, left panel). On the other hand, no such band was detected in mock treated mice (FIG. 17B, lanes 1-2, left panel). Finally, mice that received only the PTM (targeting endogenous target) also showed the presence of a 30 kDa HPV16 anti-E7 scFv (FIG. 17C, lanes 1-2). These results clearly show: (a) successful and accurate trans-splicing of mouse albumin PTM into a mouse albumin target pre-mRNA, (b) production of HPV16 anti-E7 scFv through trans-splicing. In addition, the above results further validate the targeting strategy of the present invention for the production of therapeutic antibody polypeptides and fragments thereof in vivo.

Example 5

Double Chain Antibody Production

The PTM cassettes of the present invention also may be used to produce antibodies containing both the light and heavy chain. As illustrated in FIG. 6, the bicistronic PTM cassette is similar to the HPV-16 E7 scFv PTM shown in FIG. 15A, except that it may contain, after the coding domain for the single chain antibody sequence, the 2A self-cleaving oligo peptide derived from Foot and Mouth Disease Virus (FMDV) (Fang et al., *Nature Biotechnol,* 23: 584, 2005, the disclosure of which is hereby incorporated by reference) or the encephlomayocardities (ECMV) internal ribosome entry site (IRES) (Martienz-Salas, *Curr Opin Biotechnol,* 10: 458, 1999, the disclosure of which is hereby incorporated by reference) sequence followed by the full length coding sequence to induce high levels of translation of the second chain. The use of the 2A oligo peptide and/or the IRES sequence to express the second transgene has been well documented (Fang et al., *Nature Biotechnol,* 23: 584, 2005; Martienz-Salas, *Curr Opin Biotechnol,* 10: 458, 1999). In addition, PTMs encoding single chain and the second chain (separate PTMs) could also be used for the production of double chain antibodies.

The present invention also provides a pack or kit comprising one or more containers filled with one or more of the ingredients of the compositions of the invention. The pack or kit may include a notice in the form prescribed by a governmental agency regulating the manufacture, use or sale of pharmaceuticals or biological products, which notice reflects approval by the agency of manufacture, use or sale for human administration.

The present invention is not to be limited in scope by the specific embodiments or examples described herein. Indeed, various modifications of the invention in addition to those described herein will become apparent to those skilled in the art from the foregoing description and accompanying Figures. Such modifications are intended to fall within the scope of the appended claims. Various references are cited herein, the disclosures of which are incorporated by reference in their entireties.

We claim:

1. An isolated cell comprising a chimeric RNA molecule that encodes an antibody polypeptide wherein said chimeric RNA molecule comprises:
   a) one or more target binding domains that target binding of a nucleic acid molecule that encodes the antibody polypeptide to an albumin pre-mRNA within the cell;
   b) a splice region;
   c) a spacer region that separates the splice region from the target binding domain; and
   d) a nucleotide sequence encoding the antibody polypeptide to be trans-spliced to the target albumin pre-mRNA;
   wherein said chimeric RNA molecule is recognized by nuclear splicing components within the cell.

2. The isolated cell of claim 1 wherein the antibody polypeptide is selected from the group consisting of an Ig heavy chain, an Ig light chain, an Ig Fv fragment, an Ig Fab fragment, an Ig Fc fragment, a single chain antibody and combinations thereof.

3. The isolated cell of claim 1 wherein the antibody polypeptide is a single chain antibody.

4. The cell of claim 1 wherein the antibody polypeptide comprises an Ig heavy chain and an Ig light chain.

5. The isolated cell of claim 1 wherein the antibody polypeptide is specific for a tumor specific or tumor associated antigen.

6. The isolated cell of claim 1 wherein the antibody polypeptide is specific for a microbial or autoantigen associated antigen.

7. The isolated cell of claim 6 wherein the microbial associated antigen is selected from the group consisting of viral and yeast antigens.

8. The isolated cell of claim 1 wherein the nucleic acid molecule further comprises a sequence encoding a cytokine or a growth factor.

9. An isolated cell comprising a chimeric RNA molecule that encodes an antibody polypeptide wherein said chimeric RNA molecule comprises:
   a) one or more target binding domains that target binding of a nucleic acid molecule that encodes the antibody polypeptide to an albumin pre-mRNA within the cell;
   b) a splice region;
   c) a spacer region that separates the splice region from the target binding domain; and
   d) a nucleotide sequence encoding the antibody polypeptide to be trans-spliced to the albumin pre-mRNA;
   wherein said chimeric RNA molecule is at an effective physiological and clinical level for production of antibody polypeptides and is recognized by nuclear splicing components within the cell.

10. The isolated cell of claim 9 wherein the antibody polypeptide is selected from the group consisting of an Ig heavy chain, an Ig light chain, an Ig Fv fragment, an Ig Fab fragment, an Ig Fc fragment, a single chain antibody and combinations thereof.

11. The isolated cell of claim 9 wherein the antibody polypeptide is a single chain antibody.

12. The isolated cell of claim 9 wherein the antibody polypeptide comprises an Ig heavy chain and an Ig light chain.

13. The isolated cell of claim 9 wherein the antibody polypeptide is specific for a tumor specific or tumor associated antigen.

14. The isolated cell of claim 9 wherein the antibody polypeptide is specific for a microbial or autoantigen associated antigen.

15. The isolated cell of claim 14 wherein the microbial associated antigen is selected from the group consisting of viral and yeast antigens.

16. The isolated cell of claim 9 wherein the nucleic acid molecule further comprises a sequence encoding a cytokine or a growth factor.

* * * * *